US012773469B2

(12) United States Patent
Oklu et al.

(10) Patent No.: US 12,773,469 B2
(45) Date of Patent: Oct. 27, 2026

(54) METHODS AND MATERIALS FOR EMBOLIZATION

(71) Applicants: MAYO FOUNDATION FOR MEDICAL EDUCATION AND RESEARCH, Rochester, MN (US); THE REGENTS OF THE UNIVERSITY OF CALIFORNIA, Oakland, CA (US); BOSTON SCIENTIFIC SCIMED, INC., Maple Grove, MN (US)

(72) Inventors: Rahmi Oklu, Chandler, AZ (US); Alireza Khademhosseini, Los Angeles, CA (US); Ehsan Jabbarzadeh, Columbia, SC (US)

(73) Assignees: Mayo Foundation for Medical Education and Research, Rochester, MN (US); The Regents of the University of California, Oakland, CA (US); Boston Scientific Scimed, Inc., Maple Grove, MN (US)

( * ) Notice: Subject to any disclaimer, the term of this patent is extended or adjusted under 35 U.S.C. 154(b) by 614 days.

(21) Appl. No.: 18/044,357

(22) PCT Filed: Sep. 2, 2021

(86) PCT No.: PCT/US2021/048821

§ 371 (c)(1),
(2) Date: Mar. 7, 2023

(87) PCT Pub. No.: WO2022/055785

PCT Pub. Date: Mar. 17, 2022

(65) Prior Publication Data

US 2023/0321316 A1 Oct. 12, 2023

Related U.S. Application Data

(60) Provisional application No. 63/075,598, filed on Sep. 8, 2020.

(51) Int. Cl.
*A61L 24/00* (2006.01)
*A61L 24/02* (2006.01)

(52) U.S. Cl.
CPC ......... *A61L 24/0005* (2013.01); *A61L 24/001* (2013.01); *A61L 24/0068* (2013.01); *A61L 24/02* (2013.01); *A61L 2400/06* (2013.01); *A61L 2400/12* (2013.01); *A61L 2430/36* (2013.01)

(58) Field of Classification Search
CPC ............... A61L 24/0005; A61L 24/001; A61L 24/0068; A61L 24/02; A61L 2400/06; A61L 2400/12; A61L 2430/36
See application file for complete search history.

(56) References Cited

U.S. PATENT DOCUMENTS

| | | | | |
|---|---|---|---|---|
| 5,614,204 | A * | 3/1997 | Cochrum | A61B 17/12186 128/DIG. 22 |
| 2016/0144068 | A1 | 5/2016 | Gaharwar | |
| 2018/0071446 | A1 | 3/2018 | Yeh et al. | |
| 2018/0078661 | A1* | 3/2018 | Weng | A61K 31/137 |
| 2020/0123485 | A1* | 4/2020 | Tamayol | C12M 33/00 |
| 2020/0390804 | A1 | 12/2020 | Abduljauwad et al. | |

FOREIGN PATENT DOCUMENTS

| | | | | |
|---|---|---|---|---|
| WO | 98-03203 A1 | 1/1998 | | |
| WO | 2014205261 A1 | 12/2014 | | |
| WO | WO 2014/205261 * | 12/2014 | | A61L 15/32 |
| WO | 2017069822 A2 | 4/2017 | | |

OTHER PUBLICATIONS

Buell et al., "Optimizing the Management of Aneurysmal Subarachnoid Hemorrhage: Lessons Learned and Future Directions," Journal Of Neurosciences in Rural Practice, vol. 5, Issue 2, Apr.-Jun. 2014.
Dohan et al., "Platelet-Rich Fibrin (PRF): A Second-Generation Platelet Concentrate. Part I: Technological Concepts and Evolution," Oral Surg Oral Med Oral pathol Oral Radiol Endod OOOOE, vol. 101, pp. E37-44, 2006.
Erezuma et al., "Nanoclay Reinforced Biomaterials for Mending Muscoskeletal Tissue Disorders," Advanced Healthcare Materials, 20 pages, 2100217, 2021.
Gaharwar et al., "2D Nanoclay for Biomedical Applications: Regenerative Medicine, Therapeutic Delivery, and Additive Manufacturing," Advanced Materials, 28 pages, 1900332, 2019.
Ghanaati et al., "Advanced Platelet-Rich Fibrin: A New Concept for Cell-Based Tissue Engineering by Means of Inflammatory Tissue Engineering by Means of Inflammatory Cells," Journal of Oral Implantology, vol. 40, Issue 6, pp. 679-689, Dec. 2014. (Abstract).
Hu et al., "Advances in Biomaterials and Technologies for Vascular Embolization," Advanced Materials, vol. 31, Issue 33, 1901071, Jun. 6, 2019. (Abstract).
Lubarsky et al., "Embolization Agents—Which One Should Be Used When? Part 1: Large-Vessel Embolization," Seminars in Interventional Radiology, vol. 26, No. 4, pp. 352-357, 2009.
Poursaid et al., "Polymeric Materials for Embolic and Chemoembolic Applications," Journal Of Control Release, vol. 240, pp. 414-433, Oct. 28, 2016.
Simon et al., "Complete Angiographic Obliteration of Intracranial AVMs with Endovascular Embolization: Incomplete Embolic Nidal Opacification is Associated with AVM Recurrance," Journal of Neurointerventional Surgery, vol. 2, No. 3, pp. 202-207, Sep. 2, 2010. (Abstract).
Sodhi et al., "The Clinical Profile, Management, and Overall Outcome of Aneurysmal Subarachnoid Hemorrhage at the Neurological Unit of a Tertiary Care Center in India," Journal of Neurosciences in Rural Practice, vol. 5, Issue 2, pp. 118-126, Apr.-Jun. 2014.

(Continued)

*Primary Examiner* — Shirley V Gembeh
(74) *Attorney, Agent, or Firm* — Seager, Tufte, & Wickhem, LLP

(57) ABSTRACT

This disclosure relates to methods and materials for embolization of one or more blood vessels (e.g., one or more arteries). For example, biomaterial compositions (e.g., BEM compositions containing PRF and one or more nanoclay materials) for embolization of one or more blood vessels (e.g., one or more arteries) within a mammal (e.g., a human) are provided.

19 Claims, 25 Drawing Sheets

(56) References Cited

OTHER PUBLICATIONS

Varela et al., "Injectable Platelet Rich Fibrin: Cell Content, Morphological, and Protein Characterization," Clinical Oral Investigations, vol. 23, No. 3, pp. 1309-1318, Mar. 2019. (Abstract).
Villaba-Rodriguez et al., Nanoclay/Polymer-based Hydrogels and Enzyme-Loaded Nanostructures for Wound Healing Applications, Gels, vol. 7, No. 59, pp. 1-13, 2021.
Zhu et al., "Endovascular Metal Devices for the treatment of Cerebrovascular Diseases," Advanced Materials, vol. 31, e1805452, 126 pages, 2019.
Shang et al. "Zeolite-fibrin clot composite as a haemostatic agent for haemophilia A," Journal of Biomaterials Applications, 2019, vol. 33, No. 10, pp. 1427-1433.
Bakhtiari et al. "Composition-dependent effects of nanoparticles on coagulation," International Society on Thrombosis and Haemostasis, 2015, vol. 13 (Suppl.2), p. 625 PO323-TUE.
Long et al. "Emerging Nanoclay Composite for Effective Hemostasis," Advanced Functional Materials, 2018, vol. 28, 1704452, pp. 1-9.
Naik et al. "Role of Platelet rich fibrin in wound healing: A critical review," Journal of Conservative Dentistry, 2013, vol. 16, No. 4, pp. 284-293.
De Almeida Barros Mourao et al. "Usefulness of platelet-rich fibrin as a hemostatic agent after dental extractions in patients receiving anticoagulant therapy with factor Xa inhibitors: a case series," Oral and Maxillofacial Surgery, 2019, vol. 23, pp. 381-386.
Sammartino et al. "Prevention of Hemorrhagic Complications After Dental Extractions Into Open Heart Surgery Patients Under Anticoagulant Therapy: The Use of Leukocyte- and Platelet-Rich Fibrin," Journal of Oral Implantology, 2011, vol. 37, No. 6, pp. 681-690.
Extended European Search Report dated Apr. 2, 2024 for European Application No. 21867388.7.

* cited by examiner

METHODS AND MATERIALS FOR EMBOLIZATION

CROSS-REFERENCE TO RELATED APPLICATIONS

The present application is a 35 U.S.C. § 371 national stage application of and claims priority to and the benefit of the filing date of international patent application PCT/US21/48821, filed Sep. 2, 2021, which claims the benefit to U.S. Provisional Patent Application No. 63/075,598, filed Sep. 8, 2020, which applications are hereby incorporated by reference herein their entireties for all purposes.

STATEMENT REGARDING FEDERAL FUNDING

This invention was made with government support under HL140951 and HL137193 awarded by the National Institutes of Health. The government has certain rights in the invention.

TECHNICAL FIELD

This disclosure relates to methods and materials for embolization of one or more blood vessels (e.g., one or more arteries). For example, this disclosure provides biomaterial compositions (e.g., blood-derived embolic material (BEM) compositions) for embolization of one or more blood vessels (e.g., one or more arteries) within a mammal (e.g., a human).

BACKGROUND INFORMATION

In the early 1970s, Charles Dotter, an interventional radiologist, performed the first catheter directed embolization using clots derived from patient's own blood to treat an acutely bleeding artery of the stomach (Lubarsky et al., *Intervent. Radiol.,* 26:352 (2009); Poursaid et al., *J. Controlled Release,* 240:414 (2016); and Hu et al., *Adv. Mater.,* 31:e1901071 (2019)). However, autologous blood clots for embolization were quickly abandoned because natural thrombolysis led to recanalization within hours to days resulting in re-bleeding. To embolize a bleeding artery today, metallic coils are pushed through catheters repeatedly until the coil mass inside the artery slows the blood and clots. These coils, however, have many drawbacks including limited efficacy in the anticoagulated or the coagulopathic patient, they produce significant imaging artifacts limiting evaluation of the adjacent soft tissue, when deployed they are not designed to be retrievable, and are not cost-effective (Buell et al., *J. Neurosci. Rural Pract.,* 5:109 (2014); Sodhi et al., *J. Neurosci. Rural Pract.,* 5:118 (2014); and Zhu et al., *Adv. Mater.,* 31:e1805452 (2019)). For example, to embolize an aneurysm, many coils are often used; in fact, in one study it was shown that the cost of embolizing an aneurysm can exceed $150,000, imposing a major cost burden to healthcare (Simon et al., *J. Neurointerv. Surg.,* 2:163 (2010)).

SUMMARY

This disclosure provides methods and materials for embolization of one or more blood vessels (e.g., one or more arteries). For example, this disclosure provides compositions (e.g., biomaterial compositions such as BEM compositions) for embolization (e.g., reversible embolization) of one or more blood vessels (e.g., one or more arteries) within a mammal (e.g., a human).

As demonstrated herein, a biomaterial composition (e.g., a BEM composition containing platelet-rich fibrin (PRF) (and/or leukocyte- and platelet-rich fibrin (leukocyte-PRF) and one or more nanoclay materials) can be rapidly prepared and delivered using clinical catheters to achieve embolization of first-order arteries such as the renal artery and iliac artery. As also demonstrated herein, embolization using a radiopaque BEM composition (e.g., a BEM composition containing PRF (and/or leukocyte-PRF), one or more nanoclay materials, and one or more radiopaque agents such as ethiodized oil) can be administered to a mammal (e.g., a human) and visualized in vivo.

Having the ability to perform embolization within a blood vessel of a mammal (e.g., a human) by delivering a BEM composition containing PRF (and/or leukocyte-PRF) and one or more nanoclay materials provides a unique and unrealized opportunity to achieve hemostasis of one or more blood vessels safely and quickly within a mammal. For example, a BEM composition containing PRF (and/or leukocyte-PRF) and one or more nanoclay materials can be used to treat bleeding such as hemorrhage and/or wounds. For example, using clinical catheters to deliver a BEM composition containing PRF (and/or leukocyte-PRF) and one or more nanoclay materials provided herein for embolization can be prepared at the point-of-care (e.g., using a patient's own blood), and is efficient, effective, safe, and/or cost-effective.

Further, having the ability to visualize a BEM composition containing PRF (and/or leukocyte-PRF), one or more nanoclay materials, and one or more contrast agents (e.g., radiopaque contrast agents) delivered to a mammal (e.g., a human) provides a unique and unrealized opportunity to monitor the location and efficacy of the BEM composition within a mammal.

In general, one aspect of this disclosure features compositions including (a) platelet-rich fibrin (PRF) or leukocyte-PRF, and (b) one or more nanoclay materials. The composition can include the PRF and the leukocyte-PRF. The composition can include from about 0.1 wt % to about 90 wt % of the PRF. The composition can include from about 0.1 wt % to about 90 wt % of the leukocyte-PRF. The composition can include from about 0.4 to about 0.8 wt % of the PRF. The composition can include from about 1.2 to about 1.6 wt % of the PRF. The composition can include from about 2.2 to about 2.6 wt % of the PRF. The composition can include from about 0.5 wt % to about 90 wt % of the nanoclay material. The can include from about 6.4 to about 6.8 wt % of the nanoclay material. The nanoclay material can be a silicate nanoclay. The composition also can include a radiopaque contrast agent. The composition can include from about 0.1 wt % to about 90 wt % of the radiopaque contrast agent. The composition can include from about 10 to about 40 wt % of the radiopaque contrast agent. The radiopaque contrast agent can be ethiodized oil, iohexol, gadobutrol, iron oxide nanoparticles, zinc oxide nanoparticles, magnesium oxide particles, or tantalum particles. The viscosity of the composition can decrease under a shear rate of about $10^{-2}$ 1/second. The composition can have a displacement pressure of from about 85 kPa to about 200 kPa. The mammal can be a human. The delivery can be a catheter-directed delivery. The delivery can include from about 1 cc to about 10 cc of the composition.

In another aspect, this disclosure features methods for embolization of a blood vessel within a mammal. The methods can include, or consist essentially of, delivering, to a blood vessel within a mammal, a composition that includes (a) PRF or leukocyte-PRF and (b) one or more nanoclay materials. The mammal can be a human. The delivery can be a catheter-directed delivery. The delivery can include from about 1 cc to about 10 cc of the composition.

In another aspect, this disclosure features methods for reducing blood flow in a blood vessel within a mammal. The methods can include, or consist essentially of, delivering, to a blood vessel within a mammal, a composition that includes (a) PRF or leukocyte-PRF and (b) one or more nanoclay materials. The blood flow in the blood vessel can be reduced to less than about 1 mL/second. The mammal can be a human. The delivery can be a catheter-directed delivery. The delivery can include from about 1 cc to about 10 cc of the composition.

In another aspect, this disclosure features methods for inducing blood clotting within a mammal. The methods can include, or consist essentially of, delivering, to a mammal, a composition that includes (a) PRF or leukocyte-PRF and (b) one or more nanoclay materials, where the composition can be effective to induce clotting at the delivery site. The clotting can be induced in less than about 10 minutes following the delivery. The mammal can be an anticoagulated mammal or a coagulopathic mammal. The mammal can be a human. The delivery can be a catheter-directed delivery. The delivery can include from about 1 cc to about 10 cc of the composition.

In another aspect, this disclosure features methods for inducing collagen deposition within a mammal. The methods can include, or consist essentially of, delivering, to a mammal, a composition that includes (a) PRF or leukocyte-PRF and (b) one or more nanoclay materials, where the composition can be effective to induce collagen deposition at the delivery site. The mammal can be a human. The delivery can be a catheter-directed delivery. The delivery can include from about 1 cc to about 10 cc of the composition.

In another aspect, this disclosure features methods for inducing angiogenesis within a mammal. The methods can include, or consist essentially of, delivering, to a mammal, a composition that includes (a) PRF or leukocyte-PRF and (b) one or more nanoclay materials, where the composition can be effective to induce angiogenesis at the delivery site. The mammal can be a human. The delivery can be a catheter-directed delivery. The delivery can include from about 1 cc to about 10 cc of the composition.

In another aspect, this disclosure features methods for inducing cellular proliferation within a mammal. The methods can include, or consist essentially of, delivering, to a mammal, a composition that includes (a) PRF or leukocyte-PRF and (b) one or more nanoclay materials, where the composition can be effective to induce cellular proliferation at the delivery site. The mammal can be a human. The delivery can be a catheter-directed delivery. The delivery can include from about 1 cc to about 10 cc of the composition.

In another aspect, this disclosure features methods for treating a wound within a mammal. The methods can include, or consist essentially of, delivering, to a wound within a mammal, a composition that includes (a) PRF or leukocyte-PRF and (b) one or more nanoclay materials. The wound can be a cutaneous wound. The wound can be an ulcer, a bed sore, a surgical skin wound, a burn, or alopecia. The mammal can be a human. The delivery can be a catheter-directed delivery. The delivery can include from about 1 cc to about 10 cc of the composition.

In another aspect, this disclosure features methods for treating a mammal having a bleeding disorder. The methods can include, or consist essentially of, delivering, to a mammal, a composition that includes (a) PRF or leukocyte-PRF and (b) one or more nanoclay materials. The bleeding disorder can be a non-traumatic hemorrhage, a traumatic hemorrhage, a ruptured aneurysm, a saccular aneurysm, a urethra-cutaneous fistula, an arteriovenous fistula, an entero-cutaneous fistula, or an enteroenteric fistula. The mammal can be a human. The delivery can be a catheter-directed delivery. The delivery can include from about 1 cc to about 10 cc of the composition.

In another aspect, this disclosure features methods for treating a mammal having a tumor. The methods can include, or consist essentially of, delivering, to a blood vessel within a mammal that is feeding a tumor within the mammal, a composition that includes (a) PRF or leukocyte-PRF and (b) one or more nanoclay materials. The tumor can be a benign tumor. The tumor can be a malignant tumor. The tumor can be a hepatic tumor, a uterine fibroid, a benign prostatic hyperplasia, a prostate tumor, a renal tumor, a breast cancer tumor, a melanoma, a stomach cancer tumor, or a pancreatic cancer tumor. The mammal can be a human. The delivery can be a catheter-directed delivery. The delivery can include from about 1 cc to about 10 cc of the composition.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

(FIG. 2A) Representative SEM images of lyophilized PRF (L-PRF), NC, and BEM and each gross appearance. (FIG. 2B) Flow curves of NC and BEMs revealing the shear thinning properties. (FIG. 2C) Thixotropy tests showing gels' recoverability under oscillating low and high strains. (FIG. 2D) Summary of gels' storage modulus, G', obtained from amplitude sweeps (n=3). (FIG. 2E) Summary of injection forces generated by NC, BEM and BEM-EO through a 5F catheter (n=3). (FIG. 2F) Graphic summary of average pressure required to displace NC, BEM, and BEM-EO in a vascular occlusion model (n=3); the black dotted line indicates physiologic pressure (120 mmHg); inset shows representative displacement pressure curves. (FIG. 2G) Graph showing relative viability of L-929 cells following 24 hours incubation with PRF, L-PRF, NC, BEM, and BEM-EO extracts (n=12). (FIG. 2H) Summary of sterility testing based on optical density at 600 nm showing no bacterial growth in BEM-EO at 24 hours or 1 week after inoculation; LB broth alone and LB broth inoculated with *E. coli* were used as negative and positive controls, respectively. (FIG. 2I) Rheological study showing enhanced ΔG' of BEM-EO in contact with blood compared to blood alone. (FIG. 2J) Images of blood clotting study showing enhanced coagulation when blood is in contact with BEM-EO and clinically used coil fibers. (FIG. 2K) Fluoroscopy images of BEM-EO loaded syringes containing varying concentrations of ethiodized oil. (FIG. 2L) Images of BEM-EO retrieval test in a 3D printed artery model showing complete removal of BEM-EO using Penumbra system. p values determined by two-way ANOVA with Tukey's multiple comparison, ns, not significant, ****p≤0.0001. Data represented as average±SEM.

(FIG. 3A) Micrographs of H&E stained cutaneous tissue sections of NC or BEM-EO injected sites at 3, 14, or 28 days post implantation (arrow heads point to the injected biomaterial; arrows denotes infiltrating cells). (FIG. 3B) Summary of average cell counts within the biomaterial region of the histology sections showing markedly higher cell infiltration in BEM-EO treated site compare to NC at day 14 after injection. (FIG. 3C) Histology images of Mason's trichrome stained cutaneous tissue sections of NC or BEM-EO injected sites at 3, 14, or 28 days post implantation (dotted line shows fibrous capsule thickness; black line shows region of cell infiltration). (FIG. 3D) Graph showing thicker cell infiltration layer in the BEM-EO treated site compare to NC at D14 after injection. (FIG. 3E) Morphometric analysis showing fibrous capsule layer around the injected biomaterial in the BEM-EO at D28 after injection as marked by dotted line in (FIG. 3C). (FIG. 3F and FIG. 3G) Reconstructed micro-CT images and volume analysis of the injected biomaterial volumes showing higher volume in the BEM-EO at D3 compared to NC and a decrease in BEM-EO volume by 28 days relative to BEM-EO at D3. Scale bar, 2 mm in micro-CT images, and 150 μm in histology images. p values determined by ANOVA with Tukey's multiple comparison, *p≤0.05, p≤0.01, *p≤0.001, ****p≤0.0001. Data are represented as average±SEM (n=4).

(FIG. 4A) Pre-embolization angiography showing patency of internal iliac artery (IIA) (white arrow). (FIG. 4P) Volumetric analysis of 3D rendered CT scans of pig kidneys at 2 weeks following renal artery embolization compared to control kidney. Scale bars, 150 μm in histology images and 1 cm on gross view images. p values determined by unpaired t-test, *p≤0.05, ns, not significant. Data are represented as average±SEM (n=4).

(FIG. 5A) 3D rendering of micro-CT scans and a corresponding histologic image of an iliac artery at 1 hour and 2 weeks following embolization with BEM-EO. These images demonstrate time dependent morphologic changes; the non-survival 1 hour group shows uniformly occluded artery that progresses to fragmentation in the 2-week group with intervening non-enhancing regions replaced by fibrotic tissue. Dotted line in specimens P4 and P8 represents the location where the axial micro-CT image and the corresponding H&E image were obtained, scale bar, 2.5 mm. (FIG. 5B) 3D total volume of BEM-EO was computed from micro-CT scans of embolized iliac arteries using segmentation software; these data showed that there was 63% reduction in biomaterial volume over two weeks. (FIG. 5C) Serial scans of BEM-EO inside a tube stored at 37° C. for 0, 3, 7, 14 and 70 days showing consistent dispersion of hypodense foci overtime (arrows indicate similar areas over time), scale bar, 2.5 mm. (FIG. 5D and FIG. 5E) Time-dependent measurement of hypodense foci and radiodensity of BEM-EO loaded in tubes obtained from five levels in each tube as it appear in the schematic. Each tube was separated into 5 compartments and the measurements were performed for each compartment, showing no significant differences over time. This suggests BEM-EO is stable and phase separation into components does not occur over time. Student's t-test was used to calculate differences in BEM-EO volume and one-way ANOVA with Tukey's multiple comparisons test was used to assess time-dependent changes on micro-CT in vitro. ****p≤0.0001, ns, not significant. Data are represented as average±SEM.

(FIG. 6A) Graph showing PDGF-B levels measured in freshly prepared PRF obtained from three different pigs. (FIG. 6B) Shear rate sweeps of pocBEMs from five different pigs showing similar viscosity profiles. (FIG. 6C) Graph showing G' of different pocBEMs determined for amplitude sweeps performed at 10 rad $s^{-1}$ (Dashed line indicates the average G' of 15685 Pa in all pocBEMs). (FIG. 6D) Thixotropy test revealing excellent recoverability of all pocBEM formulations. (FIG. 6E) Compression test showing injectability of pocBEMs with an average force of 30 N (dashed line). (FIG. 6F) $OD_{600}$ measurements obtained at 1 day and 1 week following inoculation with pocBEMs prepared under sterile conditions, showing no bacterial growth. (FIG. 6G) Rheological study showing rapid increase in ΔG' when blood is in contact with pocBEM compared to blood alone. (FIG. 6H) Representative test of thrombogenic potential of pocBEM showing accelerated clotting time compared to blood alone. p values were determined by two-way ANOVA with Tukey's multiple comparison, ns, not significant, $^{****}p\leq0.0001$. Data are represented as average±SEM.

(FIG. 7A) Angiogram of the pig iliac arteries showing patent internal iliac arteries (IIAs). (FIG. 7B) Digital subtraction angiography (DSA) following embolization of right IIA (RIIA) using pocBEM, showing complete occlusion. (FIG. 7C) DSA following embolization of both IIAs using pocBEM showing interruption of blood flow into both IIAs. (FIG. 7D) Micro-CT images of embolized IIAs on coronal and transverse planes (dashed line indicates the location of transverse plane). pocBEM fills the RIIA and LIIA completely without imaging artifacts. (FIG. 7E) Angiographic images showing normal blood flow into iliac arteries. (FIG. 7F) Angiographic image following coil embolization of the LIIA showing failure to stop blood flow in an anticoagulated pig. (FIG. 7G) Angiographic image demonstrates rescue of unsuccessful coil embolization in F following pocBEM injection through the catheter resulting in complete occlusion. (FIG. 7H) Angiographic image of LIIA showing normal blood flow through the coils inside the IIA following pocBEM retrieval using the Penumbra Aspiration system. (FIG. 7I) Coronal and axial micro-CT images of LIIA where coil embolization and retrieval of pocBEM was performed (dashed line shows corresponding axial section below) showing extensive streak artifacts caused by coil. LIIA did not demonstrate opacification suggesting successful aspiration of pocBEM. (FIG. 7J) Angiographic images showing unsuccessful renal artery embolization with coils in an anticoagulated pig as depicted in the schematic image to the right. (FIG. 7K) Failed coil embolization in J was successfully embolized with pocBEM; there is now absence of blood flow to the kidney. (FIG. 7L) Micro-CT image of embolized kidney showing pocBEM filling the renal artery proximal to the coil mass, which causes significant streaking artifact.

(FIG. 8A) Images of pig blood aliquots showing PRF in the upper phase following centrifugation in glass tubes. (FIG. 8B and FIG. 8C) Plots showing 43±5.3 wt % weight yield of PRF from whole blood and 7.3±0.84 wt % weight yield of L-PRF from PRF preparations.

(FIG. 9A) Image of SDS-PAGE showing PRF and L-PRF from three different pigs, and pooled L-PRF samples showing similar protein fractions. (FIG. 9B) Western blot detection of VEGF, PDGF-B, and TGF-β proteins in PRF and L-PRF. (FIG. 9C and FIG. 9D) Quantitative analysis of PDGF-B and VEGF-A protein levels in three L-PRF preparations. (FIG. 9E) Effect of PRF and L-PRF on L-929 cells proliferation in vitro at day 1 and day 3, showing enhanced cellular proliferation in the PRF and L-PRF treated cells compared to control (n=8). (FIG. 9F) Representative images of in vitro scratch assay obtained at 1 day after incubating the L929 cells with serum-free media (control), PRF, and L-PRF. (FIG. 9G) Effect of PRF, and L-PRF on L-929 migration, showing enhanced cell migration in PRF and L-PRF treated cells compared to negative control (n=6). p values determined by one-way ANOVA with Tukey's multiple comparison, $^{*}p\leq0.05$, $^{}p\leq0.01$, $^{**}p\leq0.0001$. Data are represented as average±SEM.

(FIG. 11A) Gross appearance of NC, BEM and BEM-EO aliquots. Fluoroscopic image of NC, BEM and BEM-EO showing marked x-ray enhancement in the BEM-EO syringe. (FIG. 11B) Syringes loaded with BEM or BEM-EO to be used for in vitro and in vivo experiments. (FIG. 11C) Flow curves of NC, BEM and BEM-EO revealing the shear thinning properties. (FIG. 11D) Summary of biomaterials' storage modulus, G', obtained from amplitude sweeps (n=3). (FIG. 11E) Schematic of displacement pressure measuring system. Data are represented as average±SEM.

(FIG. 14A) Representative H&E, or Mason's trichrome stained tissue sections and micro-CT images obtained from explanted skin tissues at 3, 14, or 28 days post injection with BEM (arrow heads and dashed area show injected biomaterial; arrows denote infiltrating cells in histology sections). (FIG. 14B) Summary of average cell counts within the BEM zone in histology sections showing increase in infiltrating cell number peaking at D14 in BEM and BEM-EO compared to NC. (FIG. 14C) Graph showing cell infiltration layer thickness (fibroblast rich zone) measured in Masson's trichrome stained sections. (FIG. 14D) Summary of the fibrous capsule thickness surrounding the biomaterial and the surrounding tissue. (FIG. 14E) Graph showing micro-CT volumetric analysis of injected biomaterials showing decrease in BEM and BEM-EO volume at D28. Scale bar, 2 mm in micro-CT images, and 150 μm in histology images. p values determined by ANOVA with Tukey's multiple comparison, $^{*}p\leq0.05$, $^{}p\leq0.01$, $^{*}p\leq0.001$, $^{****}p\leq0.0001$. Data are represented as average±SEM (n=4).

(FIG. 15A) Representative images of PCNA immunostained rat skin sections obtained at day 3, 14, and 28 following subcutaneous injection of NC, BEM, BEM-EO visualizing proliferating cells in brown (black arrows). (FIG. 15B) Summary of PCNA positive cell count showing higher number of proliferating cells in BEM compared to NC at day 14 and 28. (FIG. 15C) Representative images of CD31 immunostained rat skin sections obtained at day 3, 14, and 28 following subcutaneous injection of NC, BEM, or BEM-EO visualizing vessels (Black arrows). (FIG. 15D) Summary of CD31 positive vessel counts showing enhanced angiogenesis with BEM and BEM-EO compared to NC at D28. Scale bar, 150 μm. Statistical analysis was calculated using two-way ANOVA with Tukey's multiple comparison, $^{*}p\leq0.05$, $^{}p\leq0.01$, $^{*}p\leq0.001$, $^{****}p\leq0.0001$. Data presented as average±SEM.

(FIG. 18A and FIG. 18B) H & E stained IIA section showing complete casting of the arterial lumen with BEM-EO with a concentric inflammatory reaction zone that occupies approximately 40% of the luminal area (bracket). (FIG. 18C) High power histology section obtained from the concentric zone showing fat droplets (black arrows) appearing in the presence of highly abundant macrophages. (FIG. 18D) High power histology image obtained from the concentric zone showing scattered multinucleated giant cells (black arrow). Scale bars, 100 μm.

(FIG. 20A) H&E stained histology section of renal parenchyma obtained at 1 hour following embolization (insets indicate the location where high power images were taken). (FIG. 20B) Histology images showing normal renal parenchyma. (FIG. 20C and FIG. 20D) High power histology images showing embolized segmental arteries (black arrows) in trichrome stained sections. (FIG. 20E) H&E histology image of renal parenchyma obtained at two weeks following renal artery embolization. (FIG. 20F, FIG. 20G, FIG. 20H) High power histology images of areas enclosed by black squares reveal diffused necrosis in renal parenchyma occluded and fibrotic segmental renal arteries in trichrome stained images (arrows). Scale bars in A and E are 1 mm.

(FIG. 21A) Schematic presentation of pocBEM structure. (FIG. 21B) H&E image of pocBEM shows the presence of white blood cells (white arrow) and platelets (black arrow). (FIG. 21C) SEM image of pocBEM shows fibrin (white arrow) in a porous structure.

(FIG. 22A) Visibility of pocBEM in the iliac artery under fluoroscopy. (FIG. 22B, FIG. 22C) Axial and coronal micro-CT images of embolized iliac artery with pocBEM. (FIG. 22D, FIG. 22E) H&E image of embolized iliac artery showing amorphous pocBEM uniformly occluding the arterial lumen. (FIG. 22F) Before embolization DSA image showing patency of the renal artery. (FIG. 22G) Following renal artery embolization using pocBEM, DSA image shows occluded renal artery (white arrows) and absence of any flow to the kidney (dotted white line). (FIG. 22H) Micro-CT image of the embolized kidney showing hyperdense pocBEM filling the renal artery and its segmental branches without any imaging artifact. (FIG. 22I) H&E image of the embolized kidney. High power image shows embolized artery in the renal parenchyma.

(FIG. 23A) Pre-embolization angiography showing patency of renal artery segmental branches. (FIG. 23B) Digital subtraction angiography (DSA) after renal injury using 20 cm and 18 G needle (black arrow), showing extravasation of the contrast agent and pseudoaneurysms (white arrow). (FIG. 23C) DSA following embolization of renal artery using pocBEM (black arrow) showing absence of bleeding in injured area (dashed area). (FIG. 23D) DSA image before renal injury showing patency of the renal artery. (FIG. 23E) Following renal injury, DSA image shows extravasation of contrast agent and pseudoaneurysms (arrows). (FIG. 23F) DSA following embolization of injured renal arteries showing no bleeding (dashed area). (FIG. 23G and FIG. 23H) Angiographic images showing bleeding arterial pseudoaneurysms (arrows) following injury. (FIG. 23I) DSA image showing absence of bleeding after embolization with pocBEM (arrow). (FIG. 23J and FIG. 23K) DSA images showing bleeding pseudoaneurysm (black arrow) after injury created with needle to an external iliac artery branch. (FIG. 23L) DSA image showing bleeding control following embolization with pocBEM (black arrow).

DETAILED DESCRIPTION

Figure 1:
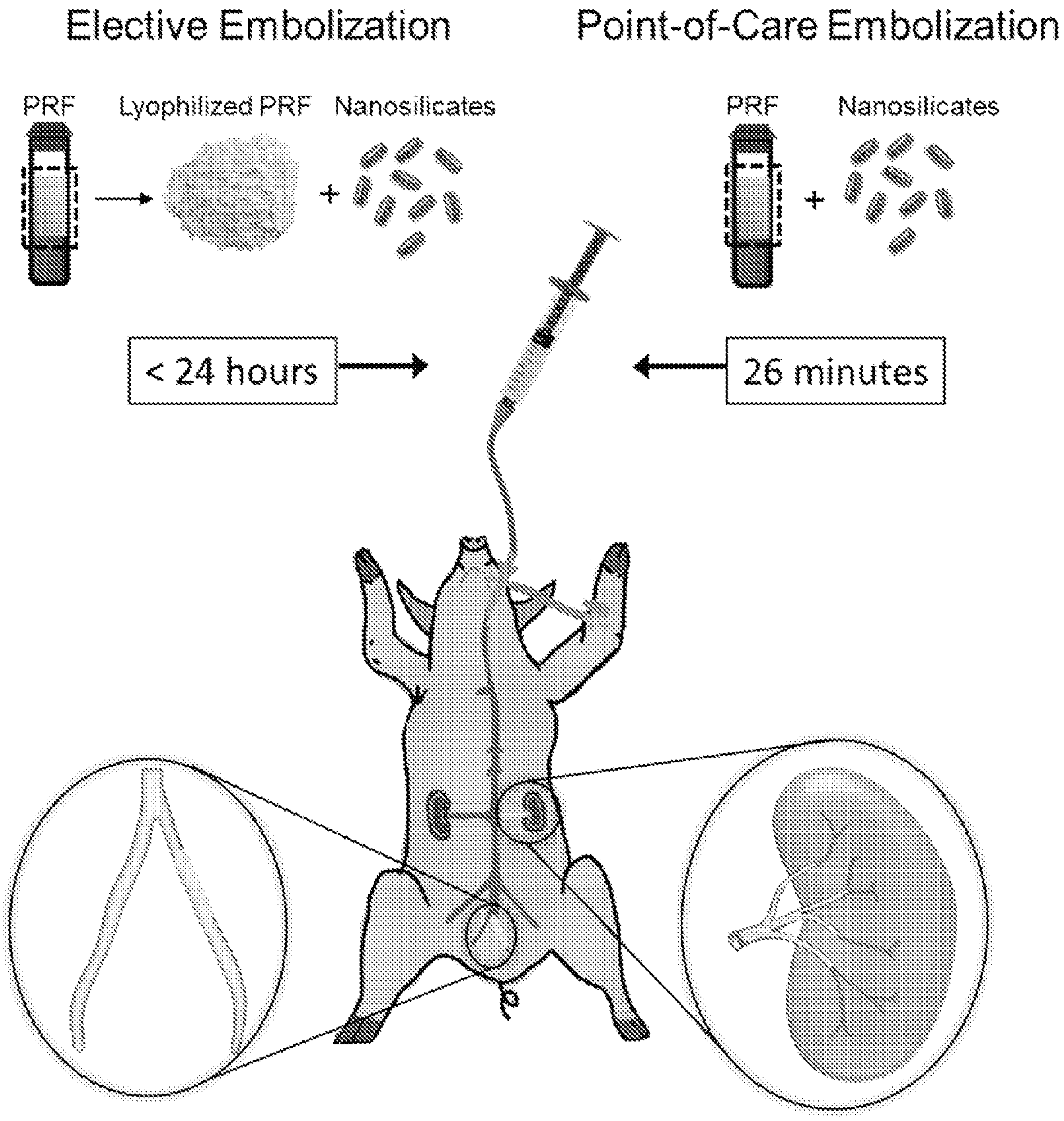
FIG. 1. Fabrication of an exemplary blood-derived embolic material (BEM) for transarterial embolization. Schematic shows the components of two types of BEM. For elective procedures, PRF can be derived from blood that is lyophilized for long-term storage at 4° C. When needed for an endovascular procedure, PRF can be mixed with nanoclay to produce BEM. For urgent or emergency type procedures, purified PRF can be mixed with nanoclay to produce the point-of-care BEM; in this form, it can be prepared rapidly and used immediately (e.g., to embolize the renal or the iliac artery).

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the aspects of the techniques and procedures described or referenced herein are well understood and commonly employed by those skilled in the art. The following text discusses various embodiments of the invention.

This disclosure provides methods and materials for embolization of one or more blood vessels (e.g., one or more arteries) within a mammal (e.g., a human). For example, this disclosure provides compositions (e.g., biomaterial compositions such as BEM compositions containing PRF (and/or leukocyte-PRF) and one or more nanoclay materials) that can be delivered to one or more blood vessels (e.g., one or more arteries) within a mammal (e.g., a human) for embolization of the blood vessel(s). In some cases, one or more compositions (e.g., biomaterial compositions) provided herein can be delivered to one or more blood vessels within a mammal (e.g., a human) to induce formation of a thrombus (e.g., an artificial embolus) within the blood vessel(s). In some cases, one or more compositions (e.g., biomaterial compositions) provided herein can be delivered to one or more blood vessels within a mammal (e.g., a human) to form an embolus (e.g., an artificial embolus) within the blood vessel(s). In another aspect, this disclosure provides compositions (e.g., biomaterial compositions such as BEM compositions containing PRF (and/or leukocyte-PRF) and one or more nanoclay materials) that can be delivered to one or more wounds (e.g., skin wounds, mucosal wounds, and/or gastrointestinal wounds) of a mammal (e.g., a human) to treat the wound (e.g., to promote wound healing).

A composition provided herein (e.g., a BEM composition) can include PRF and one or more nanoclay materials. As is known in the art, nanoclay materials such as Laponite® nanoclays are nanosize silicate particles having nanopores. These clays can be classified into four major groups: the kaolinite group (zeolite or halloysite), the montmorillonite/smectite group, the illite group, and the chlorite group (see, e.g., Gaharwar et al., Adv Mater. 2019 June; 31(23):e1900332; Erezuma et al., Adv Healthc Mater. 2021 August; 10(16):e2100217; Villalba-Rodriguez et al., Gels. 2021 May 14; 7(2):59. doi: 10.339; and US Patent Publication Nos. 20180071446 and 20200390804, which are incorporated herein by reference). In some cases, a composition provided herein can be sterile. In certain cases, a composition provided herein can have anti-bacterial activity. In some cases, a composition provided herein can be bioactive. For example, a composition provided herein can be designed to include one or more therapeutic agents.

In some cases, a composition provided herein (e.g., a BEM composition) can be designed to include any appropriate amount of a biomaterial (e.g., PRF (and/or leukocyte-PRF) and one or more nanoclay materials). For example, a composition provided herein can include from about 0.1% (wt %) to about 90% (wt %) biomaterials (e.g., from about 0.1 wt % to about 80 wt %, from about 0.1 wt % to about 70 wt %, from about 0.1 wt % to about 60 wt %, from about 0.1 wt % to about 50 wt %, from about 0.1 wt % to about 40 wt %, from about 0.1 wt % to about 30 wt %, from about 0.1 wt % to about 20 wt %, from about 0.1 wt % to about 10 wt %, from about 1 wt % to about 90 wt %, from about 5 wt % to about 90 wt %, from about 10 wt % to about 90 wt %, from about 20 wt % to about 90 wt %, from about 30 wt % to about 90 wt %, from about 40 wt % to about 90 wt %, from about 50 wt % to about 90 wt %, from about 60 wt % to about 90 wt %, from about 70 wt % to about 90 wt %, from about 80 wt % to about 90 wt %, from about 0.5 wt % to about 80 wt %, from about 1 wt % to about 70 wt %, from about 2 wt % to about 60 wt %, from about 3 wt % to about 50 wt %, from about 4 wt % to about 40 wt %, from about 5 wt % to about 30 wt %, from about 6 wt % to about 20 wt %, from about 7 wt % to about 10 wt %, from about 0.5 wt % to about 5 wt %, from about 1 wt % to about 10 wt %, from about 2 wt % to about 12 wt %, from about 3 wt % to about 15 wt %, from about 4 wt % to about 20 wt %, or from about 5 wt % to about 25 wt % biomaterials). In some cases, a composition provided herein can include about 7.2 wt % biomaterials. In some cases, a composition provided herein can include about 8 wt % biomaterials. In some cases, a composition provided herein can include about 9 wt % biomaterials.

In some cases, a composition provided herein (e.g., BEM composition) can be designed to include any type of PRF and/or leukocyte-PRF. For example, PRF (or leukocyte-PRF) can be derived from the blood of a mammal to be treated as described herein. PRF and/or leukocyte-PRF can be obtained using any appropriate method. Methods for obtaining PRF can be performed as described in, for example, Example 1. In some cases, methods for obtaining PRF can be as described elsewhere (see, e.g., Dohan et al., *Oral Surg. Oral Med. Oral Pathol. Oral Radiol. Endod.,* 101(3):e37-e44 (2006), Ghanaati et al., *J. Oral Implantol.,* 40(6):679-689 (2014); and Varela et al., *Clin. Oral Investig.,* 23(3):1309-1318 (2019)). In some cases, PRF (or leukocyte-PRF) can be lyophilized. PRF (or leukocyte-PRF) can include any amount of platelets. For example, PRF (or leukocyte-PRF) can include from about 10 platelets per cubic millimeter of PRF (platelets/$mm^3$) to about $10^6$ platelets/$mm^3$ (e.g., from about 10 platelets/$mm^3$ to about $10^6$ platelets/$mm^3$, from about 10 platelets/$mm^3$ to about $10^5$ platelets/$mm^3$ from about 10 platelets/$mm^3$ to about $10^4$ platelets/$mm^3$, from about 10 platelets/$mm^3$ to about $10^3$ platelets/$mm^3$, from about 10 platelets/$mm^3$ to about 750 platelets/$mm^3$, from about 10 platelets/$mm^3$ to about 500 platelets/$mm^3$, from about 10 platelets/$mm^3$ to about 250 platelets/$mm^3$, from about 10 platelets/$mm^3$ to about 200 platelets/$mm^3$, from about 10 platelets/$mm^3$ to about 100 platelets/$mm^3$, from about 50 platelets/$mm^3$ to about $10^6$ platelets/$mm^3$, from about 100 platelets/$mm^3$ to about $10^6$ platelets/$mm^3$, from about 250 platelets/$mm^3$ to about $10^6$ platelets/$mm^3$, from about 500 platelets/$mm^3$ to about $10^6$ platelets/$mm^3$, from about 750 platelets/$mm^3$ to about $10^6$ platelets/$mm^3$, from about $10^3$ platelets/$mm^3$ to about $10^6$ platelets/$mm^3$, from about $10^4$ platelets/$mm^3$ to about $10^6$ platelets/$mm^3$, or from about $10^5$ platelets/$mm^3$ to about $10^6$ platelets/$mm^3$). In some cases, PRF (or leukocyte-PRF) can include one or more additional components (e.g., in addition to platelets and fibrin). Examples of components that can be present in PRF (or leukocyte-PRF) include, without limitation, platelets, fibrin, growth factors (e.g., transforming growth factor beta (TGF-β), platelet derived growth factor (PDGF), and vascular endothelial growth factor (VEGF)), cytokines (e.g., IL-8, TNF-α, and IL-10), adhesion molecules, coagulation factors, cells (e.g., leukocytes, fibroblasts, neutrophils, macrophages, and mesenchymal stem cells), TGF-β, and osteocalcin.

A composition provided herein (e.g., a BEM composition containing PRF (and/or leukocyte-PRF) and one or more nanoclay materials) can include any amount of PRF (and/or leukocyte-PRF). For example, a composition provided herein can include from about 0.1% (wt %) to about 90% (wt %) PRF (and/or leukocyte-PRF) (e.g., from about 0.1 wt % to about 75 wt %, from about 0.1 wt % to about 50 wt %, from about 0.1 wt % to about 40 wt %, from about 0.1 wt % to about 30 wt %, from about 0.1 wt % to about 20 wt %, from about 0.1 wt % to about 10 wt %, from about 0.1 wt % to about 8 wt %, from about 0.1 wt % to about 5 wt %, from about 0.1 wt % to about 4 wt %, from about 0.1 wt % to about 3 wt %, from about 0.1 wt % to about 2 wt %, from about 0.1 wt % to about 1 wt %, from about 0.2 wt % to about 90 wt %, from about 0.3 wt % to about 90 wt %, from about 0.4 wt % to about 90 wt %, from about 0.5 wt % to about 90 wt %, from about 0.6 wt % to about 90 wt %, from about 0.7 wt % to about 90 wt %, from about 0.8 wt % to about 90 wt %, from about 0.9 wt % to about 90 wt %, from about 1 wt % to about 90 wt %, from about 2 wt % to about 90 wt %, from about 0.2 wt % to about 50 wt %, from about 0.3 wt % to about 30 wt %, from about 0.4 wt % to about 15 wt %, from about 0.5 wt % to about 10 wt %, from about 0.6 wt % to about 8 wt %, from about 0.7 wt % to about 5 wt %, from about 0.8 wt % to about 3 wt %, from about 0.2 wt % to about 0.6 wt %, from about 0.4 wt % to about 0.8 wt %, from about 0.6 wt % to about 1 wt %, from about 0.7 wt % to about 1.1 wt %, from about 0.8 wt % to about 1.2 wt %, from about 1 wt % to about 1.4 wt %, from about 1.2 wt % to about 1.6 wt %, from about 1.4 wt % to about 1.8 wt %, from about 1.6 wt % to about 2 wt %, from about 1.8 wt % to about 2.2 wt %, from about 2 wt % to about 2.4 wt %, from about 2.2 wt % to about 2.6 wt %, from about 2.6 wt % to about 3 wt %, from about 2.8 wt % to about 3.2 wt %, from about 3 wt % to about 3.6 wt %, or from about 3.4 wt % to about 4 wt %, PRF (and/or leukocyte-PRF)). In some cases, a composition provided herein can include from about 0.4 wt % to about 0.8 wt % (e.g., about 0.6 wt %) PRF. In some cases, a composition provided herein can include from about 1.2 wt % to about 1.6 wt % (e.g., about 1.4 wt %) PRF. In some cases, a composition provided herein can include from about 2.2 wt % to about 2.6 wt % (e.g., about 2.4 wt %) PRF.

A composition provided herein (e.g., a BEM composition containing PRF (and/or leukocyte-PRF) and one or more nanoclay materials) can include any type of nanoclay material(s). In some cases, a composition can include a single type of nanoclay material. In some cases, a composition can include two or more (e.g., two, three, four, or more) types of nanoclay materials and can be in any form. For example, a nanoclay material can be a powder. In some cases, a nanoclay material can be swellable (e.g., a nanoclay material that swells to produce a gel such as a hydrogel when dispersed in a liquid such as water). In some cases, a nanoclay material can include one or more nanoparticles. Examples of nanoparticles that can be included in a nanoclay material provided herein include, without limitation, poly(d,l lactic acid) (PLA), poly(glycolic acid) (PGA), poly(d,l-lactic-co-glycolic acid) (PLGA), poly(N,N-diethylacrylamide-co-acrylic acid), poly[acrylicacid-co-poly(ethylene glycol)m-ethyl ether acrylate] (PAA-co-PEGMEA), and poly(N-isopropylacrylamide) (PNIPAm)-hectoride. Examples of nanoclay materials that can be included in a composition provided herein include, without limitation, silicate nanoclays (e.g., a phyllosilicate nanoclay such as Laponite®).

A composition provided herein (e.g., a BEM composition containing PRF (and/or leukocyte-PRF) and one or more nanoclay materials) can include any amount of nanoclay material(s). For example, a composition provided herein can include from about 0.5% (wt %) to about 90% (wt %) nanoclay material(s) (e.g., from about 0.5 wt % to about 70 wt %, from about 0.5 wt % to about 50 wt %, from about 0.5 wt % to about 30 wt %, from about 0.5 wt % to about 15 wt %, from about 0.5 wt % to about 12 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 1 wt % to about 90 wt %, from about 2 wt % to about 90 wt %, from about 3 wt % to about 90 wt %, from about 4 wt % to about 90 wt %, from about 5 wt % to about 90 wt %, from about 6 wt % to about 90 wt %, from about 7 wt % to about 90 wt %, from about 8 wt % to about 90 wt %, from about 9 wt % to about 90 wt %, from about 10 wt % to about 90 wt %, from about 15 wt % to about 90 wt %, from about 20 wt % to about 90 wt %, from about 50 wt % to about 90 wt %, from about 75 wt % to about 90 wt %, from about 1 wt % to about 75 wt %, from about 2 wt % to about 50 wt %, from about 3 wt % to about 30 wt %, from about 4 wt % to about 20 wt %, from about 5 wt % to about 15 wt %, from about 6 wt % to about 10 wt %, from about 6.4 wt % to about 6.8 wt %, from about 1 wt % to about 5 wt %, from about 2 wt % to about 6 wt %, from about 3 wt % to about 7 wt %, from about 4 wt % to about 8 wt %, from about 5 wt % to about 9 wt %, from about 6 wt % to about 10 wt %, from about 7 wt % to about 11 wt %, or from about 8 wt % to about 12 wt % nanoclay material(s)). In some cases, a biomaterial composition provided herein can include from about 6.4 wt % to about 6.8 wt % (e.g., about 6.6 wt %) nanoclay material(s).

In some cases, a composition provided herein (e.g., a BEM composition containing PRF (and/or leukocyte-PRF) and one or more nanoclay materials) can include one or more contrast agents. For example, a composition provided herein can be designed to include one or more radiopaque contrast agents. In some cases, a composition provided herein can include a single type of radiopaque contrast agent. In some cases, a composition provided herein can include two or more (e.g., two, three, four, or more) types of radiopaque contrast agents. Examples of radiopaque contrast agents that can be included in a composition provided herein include, without limitation, ethiodized oil, iohexol, iodine, magnetic resonance imaging agents (e.g., (gadobutrols such as gadovist), and metallic particles (e.g., polymeric nanoparticles containing metallic nanoparticles) such as iron oxide nanoparticles, zinc oxide nanoparticles, magnesium oxide particles, and tantalum particles.

A composition provided herein (e.g., a BEM composition containing PRF (and/or leukocyte-PRF) and one or more nanoclay materials) can include any amount of contrast agent (e.g., radiopaque contrast agent). For example, a composition provided herein can include from about 0% (wt %) to about 90% (wt %) radiopaque contrast agent(s) (e.g., from about 0.1 wt % to about 80 wt %, from about 0.1 wt % to about 70 wt %, from about 0.1 wt % to about 60 wt %, from about 0.1 wt % to about 50 wt %, from about 0.1 wt % to about 40 wt %, from about 0.1 wt % to about 30 wt %, from about 3 wt % to about 90 wt %, from about 5 wt % to about 90 wt %, from about 8 wt % to about 90 wt %, from about 10 wt % to about 90 wt %, from about 20 wt % to about 90 wt %, from about 30 wt % to about 90 wt %, from about 40 wt % to about 90 wt %, from about 50 wt % to about 90 wt %, from about 60 wt % to about 90 wt %, from about 5 wt % to about 75 wt %, from about 8 wt % to about 50 wt %, from about 10 wt % to about 40 wt %, from about 12 wt % to about 30 wt %, from about 15 wt % to about 25 wt %, from about 18 wt % to about 22 wt %, from about 5 wt % to about 15 wt %, from about 10 wt % to about 20 wt %, from about 15 wt % to about 25 wt %, from about 20 wt % to about 30 wt %, from about 25 wt % to about 35 wt %, from about 30 wt % to about 40 wt %, or from about 35 wt % to about 45 wt % radiopaque contrast agent(s)). In some cases, a composition provided herein can include about 18 to about 22 wt % radiopaque contrast agent (e.g., about 20 wt % ethiodized oil). In some cases, a composition provided herein can include about 10 to about 40 wt % radiopaque contrast agent (e.g., about 25 wt % ethiodized oil).

When a composition provided herein (e.g., a BEM composition containing PRF (and/or leukocyte-PRF) and one or more nanoclay materials) includes a contrast agent, the composition can be visualized (e.g., within a mammal) using any appropriate method. For example, imaging techniques such as ultrasound, computed tomography, magnetic resonance imaging, and/or fluoroscopy can be used to visualize a composition provided herein that includes one or more contrast agents.

In some cases, a composition provided herein (e.g., a BEM composition containing PRF (and/or leukocyte-PRF) and one or more nanoclay materials) can include about 0.6 wt % PRF and about 6.6% wt % nanoclay material(s). For example, a composition provided herein can include about 0.6 wt % PRF, about 6.6% wt % nanoclay material(s), and about 20 wt % ethiodized oil.

In some cases, a composition provided herein (e.g., a BEM composition containing PRF (and/or leukocyte-PRF) and one or more nanoclay materials) can include about 1.4 wt % PRF and about 6.6% wt % nanoclay material(s). For example, a composition provided herein can include about 1.4 wt % PRF, about 6.6% wt % nanoclay material(s), and about 25 wt % ethiodized oil.

In some cases, a composition provided herein (e.g., a BEM composition containing PRF (and/or leukocyte-PRF) and one or more nanoclay materials) can include about 2.4 wt % PRF and about 6.6% wt % nanoclay material(s). For example, a composition provided herein can include about 2.4 wt % PRF, about 6.6% wt % nanoclay material(s), and about 25 wt % ethiodized oil.

In some cases, a composition provided herein (e.g., a BEM composition containing PRF (and/or leukocyte-PRF) and one or more nanoclay materials) can be biodegradable (e.g., can biodegrade within a mammal). For example, a volume of a composition delivered to a blood vessel within a mammal (e.g., a human) can decrease over time. In some cases, a volume of a composition delivered to a blood vessel within a mammal (e.g., a human) can decrease by at least about 25% (e.g., at least about 30%, at least about 40%, at least about 50%, at least about 60%, at least about 70%, or at least about 75%) over time. In some cases, a volume of a composition delivered to a blood vessel within a mammal (e.g., a human) can decrease for about 14 days following delivery. For example, a volume of a composition delivered to a blood vessel within a mammal (e.g., a human) can decrease by at least about 60% for about 14 days following delivery. In some cases, a volume of a composition delivered to a blood vessel within a mammal (e.g., a human) can decrease for about 28 days following delivery. For example, a volume of a composition delivered to a blood vessel within a mammal (e.g., a human) can decrease by at least about 75% for about 28 days following delivery.

In some cases, when a composition provided herein (e.g., a BEM composition containing PRF (and/or leukocyte-PRF) and one or more nanoclay materials) biodegrades after being delivered to a blood vessel within a mammal (e.g., a human), the biodegraded composition can be replaced with fibrotic tissue (e.g., permanent fibrotic tissue).

In some cases, a composition provided herein (e.g., a BEM composition containing PRF (and/or leukocyte-PRF) and one or more nanoclay materials) can be a shear-thinning composition. For example, a viscosity of a composition provided herein can decrease under a shear rate of from about 0.0001 l/second to about 100 l/second (e.g., from about 0.0001 l/second to about 80 l/second, from about 0.0001 l/second to about 60 l/second, from about 0.0001 l/second to about 50 l/second, from about 0.0001 l/second to about 40 l/second, from about 0.0001 l/second to about 30 l/second, from about 0.0001 l/second to about 20 l/second, from about 0.0001 l/second to about 10 l/second, from about 0.0001 l/second to about 1 l/second, from about 0.001 l/second to about 100 l/second, from about 0.01 l/second to about 100 l/second, from about 0.1 l/second to about 100 l/second, from about 1 l/second to about 100 l/second, from about 10 l/second to about 100 l/second, from about 20 l/second to about 100 l/second, from about 30 l/second to about 100 l/second, from about 50 l/second to about 100 l/second, from about 70 l/second to about 100 l/second, from about 0.001 l/second to about 90 l/second, from about 0.01 l/second to about 80 l/second, from about 0.1 l/second to about 70 l/second, from about 1 l/second to about 60 l/second, from about 10 l/second to about 50 l/second, from about 20 l/second to about 40 l/second, from about 0.0001 l/second to about 1 l/second, from about 0.001 l/second to about 10 l/second, from about 0.01 l/second to about 20 l/second, from about 0.1 l/second to about 30 l/second, from about 1 l/second to about 40 l/second, from about 10 l/second to about 50 l/second, from about 20 l/second to about 60 l/second, from about 30 l/second to about 70 l/second, from about 40 l/second to about 80 l/second, or from about 50 l/second to about 90 l/second). In some cases, a viscosity of a composition provided herein can decrease under a shear rate of about 0.01 ($10^{-2}$) l/second.

In some cases, a composition provided herein (e.g., a BEM composition containing PRF (and/or leukocyte-PRF) and one or more nanoclay materials) can have a displacement pressure that is higher than the mean pressure of a blood vessel (e.g., a healthy blood vessel). For example, a composition provided herein can have a displacement pressure of from about 85 kPa to about 200 kPa (e.g., from about 85 kPa to about 175 kPa, from about 85 kPa to about 150 kPa, from about 85 kPa to about 125 kPa, from about 85 kPa to about 100 kPa, from about 100 kPa to about 200 kPa, from about 125 kPa to about 200 kPa, from about 150 kPa to about 200 kPa, from about 175 kPa to about 200 kPa, from about 100 kPa to about 175 kPa, from about 125 kPa to about 150 kPa, from about 85 kPa to about 125 kPa, from about 100 kPa to about 150 kPa, or from about 125 kPa to about 175 kPa).

In some cases, a composition provided herein (e.g., a BEM composition containing PRF (and/or leukocyte-PRF) and one or more nanoclay materials) can be shelf stable (e.g., does not separate during storage). In some cases, a composition provided herein can be stable at any temperature (e.g., about −20° C., about 4° C., about 25° C., or about 37° C.). For example, a composition provided herein can be stable for from about 0.1 hours to about 12 months (e.g., from about 0.1 hours to about 11 months, from about 0.1 hours to about 10 months, from about 0.1 hours to about 9 months, from about 0.1 hours to about 8 months, from about 0.1 hours to about 7 months, from about 0.1 hours to about 6 months, from about 0.1 hours to about 5 months, from about 0.1 hours to about 4 months, from about 0.1 hours to about 3 months, from about 0.1 hours to about 2 months, from about 0.1 hours to about 1 month, from about 0.1 hours to about 3 weeks, from about 0.1 hours to about 2 weeks, from about 0.1 hours to about 7 days, from about 0.1 hours to about 4 days, from about 0.1 hours to about 2 days, from about 0.1 hours to about 24 hours, from about 0.1 hours to about 12 hours, from about 0.1 hours to about 3 hours, from about 2 hours to about 12 months, from about 12 hours to about 12 months, from about 24 hours to about 12 months, from about 5 days to about 12 months, from about 2 weeks to about 12 months, from about 3 weeks to about 12 months, from about 1 month to about 12 months, from about 2 months to about 12 months, from about 3 months to about 12 months, from about 4 months to about 12 months, from about 5 months to about 12 months, from about 6 months to about 12 months, from about 7 months to about 12 months, from about 8 months to about 12 months, from about 9 months to about 12 months, from about 10 months to about 12 months, from about 1 hour to about 8 months, from about 12 hours to about 6 months, from about 24 hours to about 4 months, from about 1 week to about 3 months, from about 2 weeks to about 2 months, from about 1 hours to about 1 week, from about 1 week to about 1 months, from about 2 weeks to about 2 months, from about 3 weeks to about 3 months, from about 4 weeks to about 4 months, from about 5 weeks to about 5 months, from about 6 weeks to about 6 months, from about 7 weeks to about 7 months, from about 8 weeks to about 8 months, from about 9 weeks to about 9 months, or from about 10 weeks to about 10 months). In some cases, a composition provided herein can be stable for about 6 months (e.g., without phase separation) in a test tube. In some cases, a composition provided herein can be stable (e.g., at 37° C.) for about 70 days.

A composition provided herein (e.g., a BEM composition containing PRF (and/or leukocyte-PRF) and one or more nanoclay materials) can be made using any appropriate method. In some cases, PRF and one or more nanoclay materials can be mixed first, and then one or more radiopaque contrast agents can be added. For example, centrifugal mixing, vortex mixing, speed mixer mixing, and/or manual mixing can be used for mixing (e.g., homogenous mixing) of PRF, one or more nanoclay materials, and, optionally, one or more radiopaque contrast agents to make a composition provided herein. In some cases, a composition provided herein can be made as described in Example 1.

A composition provided herein (e.g., a BEM composition containing PRF (and/or leukocyte-PRF) and one or more nanoclay materials) can be made rapidly. In some cases, a composition provided herein can be prepared in less than about 60 minutes (e.g., less than about 55 minutes, less than about 50 minutes, less than about 45 minutes, less than about 40 minutes, less than about 35 minutes, less than about 30 minutes, less than about 25 minutes, or less than about 20 minutes). For example, a composition provided herein can be prepared in less than about 25 minutes. In some cases, a composition provided herein can be prepared in from about 10 minutes to about 24 hours (e.g., from about 10 minutes to about 12 hours, from about 10 minutes to about 10 hours, from about 10 minutes to about 8 hours, from about 10 minutes to about 1 hour, from about 10 minutes to about 45 minutes, from about 10 minutes to about 35 minutes, from about 10 minutes to about 30 minutes, from about 10 minutes to about 25 minutes, from about 20 minutes to about 24 hours, from about 30 minutes to about 24 hours, from about 60 minutes to about 24 hours, from about 15 minutes to about 12 hours, from about 20 minutes to about 8 hours, from about 25 minutes to about 4 hours, from about 10 minutes to about 25 minutes, from about 15 minutes to about 30 minutes, or from about 20 minutes to about 35 minutes).

Also provided herein are methods for using one or more compositions provided herein (e.g., a BEM composition containing PRF (and/or leukocyte-PRF) and one or more nanoclay materials). In some cases, one or more compositions provided herein (e.g., a BEM composition containing PRF (and/or leukocyte-PRF) and one or more nanoclay materials) can be used for embolization of one or more blood vessels within a mammal (e.g., a human). For example, one or more compositions provided herein can be delivered to one or more blood vessels within a mammal for embolization of the blood vessel(s). In some cases, one or more compositions provided herein can be used for embolization without fragmentation of the delivered compositions. In some cases, one or more compositions provided herein can be used for embolization without migration of the composition(s). In some cases, one or more compositions provided herein can be used for embolization having a recanalization rate of less than about 35% (e.g., less than about 30%, less than about 25%, less than about 20%, less than about 15%, or less than about 10%).

In some cases, one or more compositions provided herein (e.g., a BEM composition containing PRF (and/or leukocyte-PRF) and one or more nanoclay materials) can be delivered to one or more blood vessels within a mammal (e.g., a human) to reduce or eliminate blood flow within the blood vessel(s). For example, one or more compositions provided herein can be delivered to one or more blood vessels within a mammal (e.g., a human) to reduce blood flow within the blood vessel(s) by for example, 10, 20, 30, 40, 50, 60, 70, 80, 90, 95, or more percent. For example, one or more compositions provided herein can be delivered to one or more blood vessels within a mammal (e.g., a human) to reduce blood flow within the blood vessel(s) to less than about 1 mL/second. In some cases, one or more compositions provided herein can be delivered to one or more blood vessels within a mammal (e.g., a human) to stop blood flow within the blood vessel(s).

In some cases, one or more compositions provided herein (e.g., a BEM composition containing PRF (and/or leukocyte-PRF) and one or more nanoclay materials) can be delivered to one or more blood vessels and/or one or more wounds within a mammal (e.g., a human) to induce clotting at the delivery site. For example, one or more compositions provided herein can be delivered to one or more blood vessels and/or one or more wounds within a mammal (e.g., a human) to induce clotting at the delivery site in less than about 10 minutes (e.g., less than about 9 minutes, less than about 8 minutes, less than about 7 minutes, less than about 6 minutes, less than about 5 minutes, less than about 4 minutes, less than about 3 minutes, or less than about 2 minutes).

In some cases, one or more compositions provided herein (e.g., a BEM composition containing PRF (and/or leukocyte-PRF) and one or more nanoclay materials) can be delivered to one or more blood vessels and/or one or more wounds within a mammal (e.g., a human) to increase collagen deposition at the delivery site. For example, one or more compositions provided herein can be delivered to one or more blood vessels and/or one or more wounds within a mammal (e.g., a human) to increase collagen deposition at the delivery site by, for example, 10, 20, 30, 40, 50, 60, 70, 80, 90, 95, or more percent.

In some cases, one or more compositions provided herein (e.g., a BEM composition containing PRF (and/or leukocyte-PRF) and one or more nanoclay materials) can be delivered to one or more blood vessels and/or one or more wounds within a mammal (e.g., a human) to increase angiogenesis at the delivery site. For example, one or more compositions provided herein can be delivered to one or more blood vessels and/or one or more wounds within a mammal (e.g., a human) to increase angiogenesis at the delivery site by, for example, 10, 20, 30, 40, 50, 60, 70, 80, 90, 95, or more percent.

In some cases, one or more compositions provided herein (e.g., a BEM composition containing PRF (and/or leukocyte-PRF) and one or more nanoclay materials) can be delivered to one or more blood vessels and/or one or more wounds within a mammal (e.g., a human) to increase cellular proliferation at the delivery site. For example, one or more compositions provided herein can be delivered to one or more blood vessels and/or one or more wounds within a mammal (e.g., a human) to increase cellular proliferation at the delivery site by, for example, 10, 20, 30, 40, 50, 60, 70, 80, 90, 95, or more percent.

In some cases, one or more compositions provided herein (e.g., a BEM composition containing PRF (and/or leukocyte-PRF) and one or more nanoclay materials) can be delivered to one or more blood vessels within a mammal (e.g., a human) having a bleeding disorder (e.g., a coagulopathy) to treat the mammal. For example, a composition provided herein can be delivered to one or more blood vessels feeding one or more tumors within the mammal to reduce or eliminate blood flow associated with the bleeding disorder. Examples of bleeding disorders that can be treated as described herein (e.g., by delivering a composition including PRF and one or more nanoclay materials to one or more blood vessels within a mammal) include, without limitation, hemorrhage (e.g., non-traumatic hemorrhage and traumatic hemorrhage), aneurysms (e.g., ruptured aneurysms, and saccular aneurysms), and vascular malformations (e.g., fistulas such as urethra-cutaneous fistulas, arteriovenous fistulas, enterocutaneous fistulas, and enteroenteric fistulas).

In some cases, one or more compositions provided herein (e.g., a BEM composition containing PRF (and/or leukocyte-PRF) and one or more nanoclay materials) can be delivered to one or more blood vessels within a mammal (e.g., a human) having one or more tumors to treat the mammal. For example, a composition provided herein can be delivered to one or more blood vessels feeding one or more tumors within the mammal to reduce or eliminate blood flow to the tumor(s). In some cases, a tumor can be a malignant tumor. In some cases, a tumor can be a benign tumor. Examples of tumors that can be treated as described herein (e.g., by delivering a composition including PRF and one or more nanoclay materials to one or more blood vessels within a mammal) include, without limitation, hepatic tumors, uterine fibroids, benign prostatic hyperplasias, prostate tumors, renal tumors, breast cancer tumors, melanomas, stomach cancer tumors, and pancreatic cancer tumors. For example, one or more compositions provided herein can be delivered to one or more blood vessels feeding one or more tumors within a mammal (e.g., a human) to reduce the size (e.g., volume) of the tumor(s) by for example, 10, 20, 30, 40, 50, 60, 70, 80, 90, 95, or more percent.

In some cases, when one or more compositions provided herein (e.g., a BEM composition containing PRF (and/or leukocyte-PRF) and one or more nanoclay materials) are delivered to one or more blood vessels within a mammal (e.g., a human), the mammal can experience minimal or no complications associated with embolization. Examples of complications associated with embolization include, without limitation, vasospasm, thrombosis, dissections, and rupture.

In some cases, one or more compositions provided herein (e.g., a BEM composition containing PRF (and/or leukocyte-PRF) and one or more nanoclay materials) can be administered to a wound (e.g., a skin wound) on a mammal (e.g., a human) to accelerate wound healing within the mammal. For example, a composition provided herein can be delivered to a wound within the mammal to reduce or eliminate blood flow from the wound (e.g., to form a blood clot at the wound). A wound can affect any part of a mammal (e.g., any part of a mammal's body). In some cases, a wound can be a cutaneous wound or skin wound. Examples of wounds that can be treated as described herein (e.g., by delivering a composition including PRF and one or more nanoclay materials to one or more blood vessels within a mammal) include, without limitation, abrasion skin wounds, ulcers (e.g., chronic leg ulcers, diabetic foot ulcers, and venous leg ulcers), bed sores, surgical skin wounds, burns, and alopecia. For example, a composition described herein can be administered to a mammal having a wound to accelerate wound healing within the mammal by, for example, 10, 20, 30, 40, 50, 60, 70, 80, 90, 95, or more percent.

One or more compositions provided herein (e.g., a BEM composition containing PRF (and/or leukocyte-PRF) and one or more nanoclay materials) can be delivered to one or more blood vessels and/or one or more wounds within any type of mammal. In some cases, a mammal (e.g., a human) can be anticoagulated (e.g., can be taking one or more anticoagulants). In some cases, a mammal (e.g., a human) can be coagulopathic (e.g., can have a bleeding disorder in which the mammal's blood's ability to coagulate is impaired). Examples of mammals that can have one or more compositions provided herein delivered to one or more blood vessels and/or one or more wounds within the mammal include, without limitation, humans, non-human primates such as monkeys, dogs, cats, horses, cows, pigs, sheep, mice, rats, and rabbits.

When delivering one or more compositions provided herein (e.g., a BEM composition containing PRF (and/or leukocyte-PRF) and one or more nanoclay materials) to one or more blood vessels within a mammal (e.g., a human), the composition(s) can be delivered to any type of blood vessel within the mammal. In some cases, a blood vessel can be a diseased blood vessel. In some cases, a blood vessel can be an injured blood vessel. Examples of types of blood vessels into which a composition provided herein can be delivered include, without limitation, arteries, veins, and capillaries. When one or more compositions provided herein are delivered to an artery, the artery can be any artery within a mammal (e.g., a human) such as a renal artery, hepatic artery, splenic artery, femoral artery, brachial artery, an iliac artery, carotid artery, or cerebral artery.

When delivering one or more compositions provided herein (e.g., a BEM composition containing PRF (and/or leukocyte-PRF) and one or more nanoclay materials) to one or more blood vessels and/or one or more wounds within a mammal (e.g., a human), any appropriate method of delivery can be used. In some cases, one or more compositions provided herein can be delivered to one or more blood vessels within a mammal (e.g., a human) by injection directly into a blood vessel (e.g., a blood vessel in need of embolization). In some cases, one or more compositions provided herein can be delivered to one or more wounds within a mammal (e.g., a human) by injection directly onto a wound. In some cases, one or more compositions provided herein can be delivered to one or more blood vessels and/or one or more wounds within a mammal (e.g., a human) by catheter-directed delivery (e.g., via a catheter inserted into a blood vessel in need of embolization). When one or more compositions provided herein are delivered to one or more blood vessels and/or one or more wounds within a mammal (e.g., a human) by catheter-directed delivery any type of catheter can be used (e.g., a Bernstein catheter, a microcatheter, a Cobra catheter, a Fogarty balloon, and a ProGreat catheter). When one or more compositions provided herein are delivered to one or more blood vessels and/or one or more wounds within a mammal (e.g., a human) by catheter-directed delivery any size catheter can be used. For example, one or more compositions provided herein can be delivered to one or more blood vessels and/or one or more wounds within a mammal (e.g., a human) using a catheter having a size of from about 1.7 French to about 6 French (e.g., from about 1.7 French to about 5 French, from about 1.7 French to about 4 French, from about 1.7 French to about 3 French, from about 1.7 French to about 2 French, from about 2 French to about 6 French, from about 3 French to about 6 French, from about 4 French to about 6 French, from about 5 French to about 6 French, from about 2 French to about 5 French, from about 3 French to about 4 French, from about 2 French to about 4 French, or from about 3 French to about 5 French). For example, one or more compositions provided herein can be delivered to one or more blood vessels within a mammal (e.g., a human) using a catheter having a size of about 5 French.

One or more compositions provided herein (e.g., a BEM composition containing PRF (and/or leukocyte-PRF) and one or more nanoclay materials) can be delivered to one or more blood vessels and/or one or more wounds within a mammal (e.g., a human) at any delivery rate (e.g., can be delivered at any flow rate). For example, one or more compositions provided herein can be delivered to one or more blood vessels and/or one or more wounds within a mammal (e.g., a human) at a rate of from about 50 μL/minute to about 5000 μL/minute (e.g., from about 50 μL/minute to about 4000 μL/minute, from about 50 μL/minute to about 3000 μL/minute, from about 50 μL/minute to about 2000 μL/minute, from about 50 μL/minute to about 1000 μL/minute, from about 50 μL/minute to about 500 μL/minute, from about 50 μL/minute to about 400 μL/minute, from about 50 μL/minute to about 300 μL/minute, from about 50 μL/minute to about 200 μL/minute, from about 50 μL/minute to about 100 μL/minute, from about 100 μL/minute to about 5000 μL/minute, from about 200 μL/minute to about 5000 μL/minute, from about 300 μL/minute to about 5000 μL/minute, from about 400 μL/minute to about 5000 μL/minute, from about 500 μL/minute to about 5000 μL/minute, from about 600 μL/minute to about 5000 μL/minute, from about 700 μL/minute to about 5000 μL/minute, from about 800 μL/minute to about 5000 μL/minute, from about 900 μL/minute to about 5000 μL/minute, from about 1000 μL/minute to about 5000 μL/minute, from about 2000 μL/minute to about 5000 μL/minute, from about 3000 μL/minute to about 5000 μL/minute, from about 4000 μL/minute to about 5000 μL/minute, from about 100 μL/minute to about 4000 μL/minute, from about 200 μL/minute to about 3000 μL/minute, from about 300 μL/minute to about 2000 μL/minute, from about 400 μL/minute to about 1000 μL/minute, from about 500 μL/minute to about 750 μL/minute, from about 50 μL/minute to about 500 μL/minute, from about 100 μL/minute to about 600 μL/minute, from about 200 μL/minute to about 700 μL/minute, from about 300 μL/minute to about 800 μL/minute, from about 400 μL/minute to about 900 μL/minute, from about 500 μL/minute to about 1000 μL/minute, from about 600 μL/minute to about 2000 μL/minute, from about 700 μL/minute to about 3000 μL/minute, or from about 800 μL/minute to about 4000 μL/minute). For example, one or more compositions provided herein can be delivered to one or more blood vessels and/or one or more wounds within a mammal (e.g., a human) at a rate of from about 300 μL/minute.

Any amount of one or more compositions provided herein (e.g., BEM composition containing PRF (and/or leukocyte-PRF) and one or more nanoclay materials) can be delivered to one or more blood vessels and/or one or more wounds within a mammal (e.g., a human). For example, from about 1 cc to about 10 cc (e.g., from about 1 cc to about 9 cc, from about 1 cc to about 8 cc, from about 1 cc to about 7 cc, from about 1 cc to about 6 cc, from about 1 cc to about 5 cc, from about 1 cc to about 4 cc, from about 1 cc to about 3 cc, from about 1 cc to about 2 cc, from about 2 cc to about 10 cc, from about 3 cc to about 10 cc, from about 4 cc to about 10 cc, from about 5 cc to about 10 cc, from about 6 cc to about 10 cc, from about 7 cc to about 10 cc, from about 8 cc to about 10 cc, from about 9 cc to about 10 cc, from about 2 cc to about 9 cc, from about 3 cc to about 8 cc, from about 4 cc to about 7 cc, from about 5 cc to about 6 cc, from about 1 cc to about 3 cc, from about 2 cc to about 4 cc, from about 3 cc to about 5 cc, from about 4 cc to about 6 cc, from about 5 cc to about 7 cc, from about 6 cc to about 8 cc, or from about 7 cc to about 9 cc) of one or more compositions provided herein can be delivered to one or more blood vessels and/or one or more wounds within a mammal (e.g., a human).

In some cases, after one or more compositions provided herein (e.g., a BEM composition containing PRF (and/or leukocyte-PRF) and one or more nanoclay materials) are used for embolization of one or more blood vessels within a mammal (e.g., a human), the composition(s) can be retrieved from the blood vessel(s). For example, after one or more compositions provided herein are delivered to one or more blood vessels within a mammal for embolization of the blood vessel(s), the composition can be retrieved to increase (e.g., restore) blood flow through the blood vessel(s). Any appropriate method can be used to retrieve one or more compositions provided herein from one or move blood vessels within a mammal (e.g., a human). For example, aspiration catheters and surgical removal can be used to retrieve one or more compositions provided herein from one or move blood vessels within a mammal (e.g., a human).

In some cases, one or more compositions provided herein (e.g., a BEM composition containing PRF (and/or leukocyte-PRF) and one or more nanoclay materials) can be delivered to one or more blood vessels within a mammal (e.g., a human) as the sole active agent used for embolization.

In some cases, one or more compositions provided herein (e.g., a BEM composition containing PRF (and/or leukocyte-PRF) and one or more nanoclay materials) can be delivered to one or more blood vessels within a mammal (e.g., a human) in combination with one or more additional agents used for embolization. For example, one or more compositions provided herein can be delivered to one or more blood vessels within a mammal (e.g., a human) in combination with solid embolic materials (e.g., a coils, particles, foam, a plug, microspheres, and/or beads) and/or liquid embolic materials (e.g., butyl cyanoacrylate (n-BCA), and Onyx®).

In cases where one or more compositions provided herein (e.g., a BEM composition containing PRF (and/or leukocyte-PRF) and one or more nanoclay materials) are used in combination with additional agents used for embolization, the one or more additional agents used for embolization can be administered at the same time (e.g., in the same composition or in separate compositions) or independently. For example, one or more compositions provided herein can be administered first, and the one or more additional agents used for embolization administered second, or vice versa.

In some cases, one or more compositions provided herein (e.g., a BEM composition containing PRF (and/or leukocyte-PRF) and one or more nanoclay materials) can be delivered to one or more wounds within a mammal (e.g., a human) as the sole active agent used for wound healing.

In some cases, one or more compositions provided herein (e.g., a BEM composition containing PRF (and/or leukocyte-PRF) and one or more nanoclay materials) can be delivered to one or more wounds within a mammal (e.g., a human) in combination with one or more additional agents used for wound healing. For example, one or more compositions provided herein can be delivered to one or more wounds within a mammal (e.g., a human) in combination with antimicrobial (e.g., antibiotic, antifungal, and antiseptic) agents, recombinant growth factors, immunotherapies, chemotherapies, and/or nanoparticle therapies.

In cases where one or more compositions provided herein (e.g., a BEM composition containing PRF (and/or leukocyte-PRF) and one or more nanoclay materials) are used in combination with additional agents used for wound healing, the one or more additional agents used for wound healing can be administered at the same time (e.g., in the same composition or in separate compositions) or independently. For example, one or more compositions provided herein can be administered first, and the one or more additional agents used for wound healing administered second, or vice versa.

The invention will be further described in the following examples, which do not limit the scope of the invention described in the claims.

EXAMPLES

Example 1: Blood-Derived Biomaterial for Catheter Directed Arterial Embolization This Example describes the development of blood-derived embolic materials (BEMs) with regenerative properties that can be rapidly prepared and delivered using a clinical catheter to achieve instant and durable hemostasis regardless of coagulopathy (FIG. 1). BEMs have significant advantages over embolic materials used today, making it a promising new tool for embolization.

Figure 8:
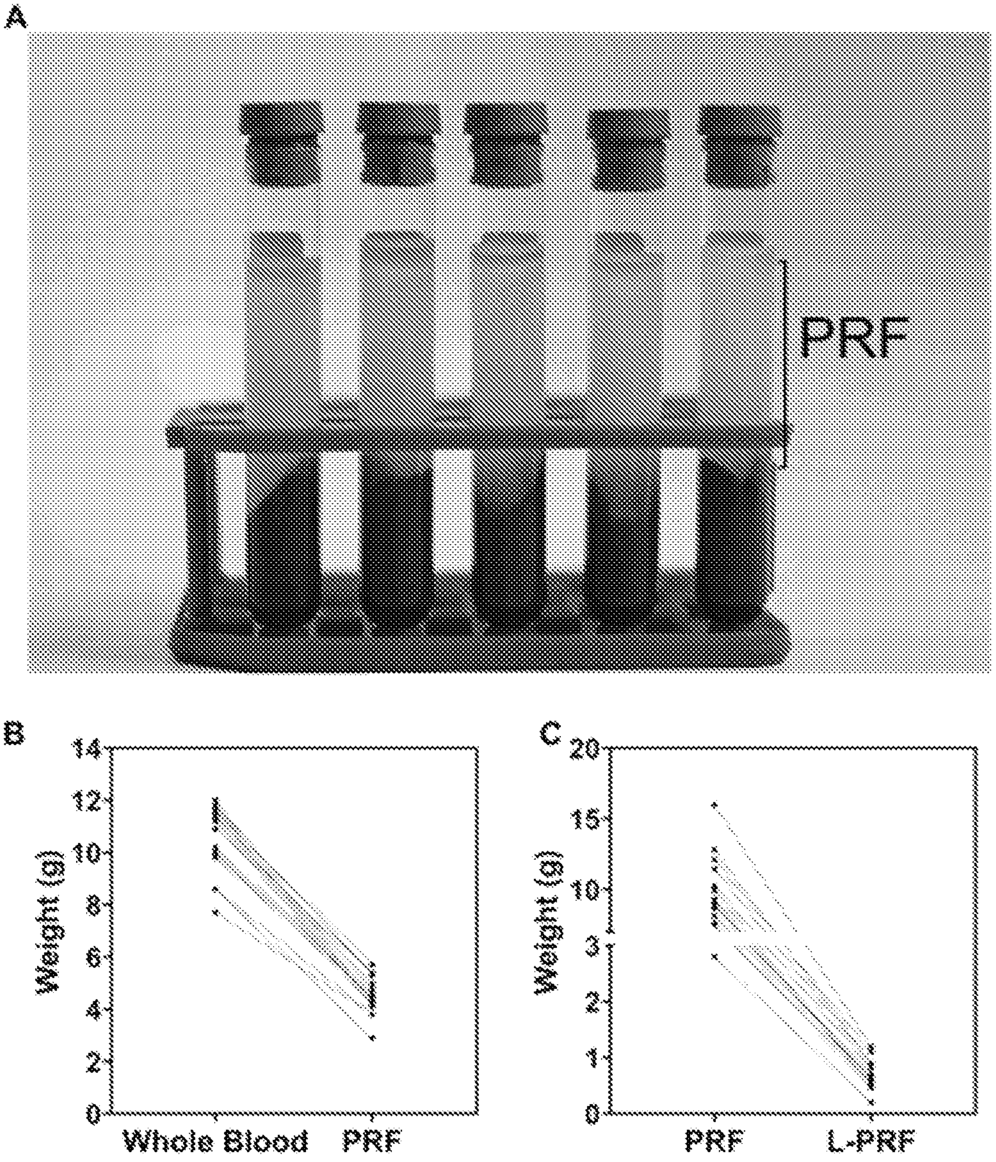
FIGS. 8A-8C. PRF preparation.
Figure 9:
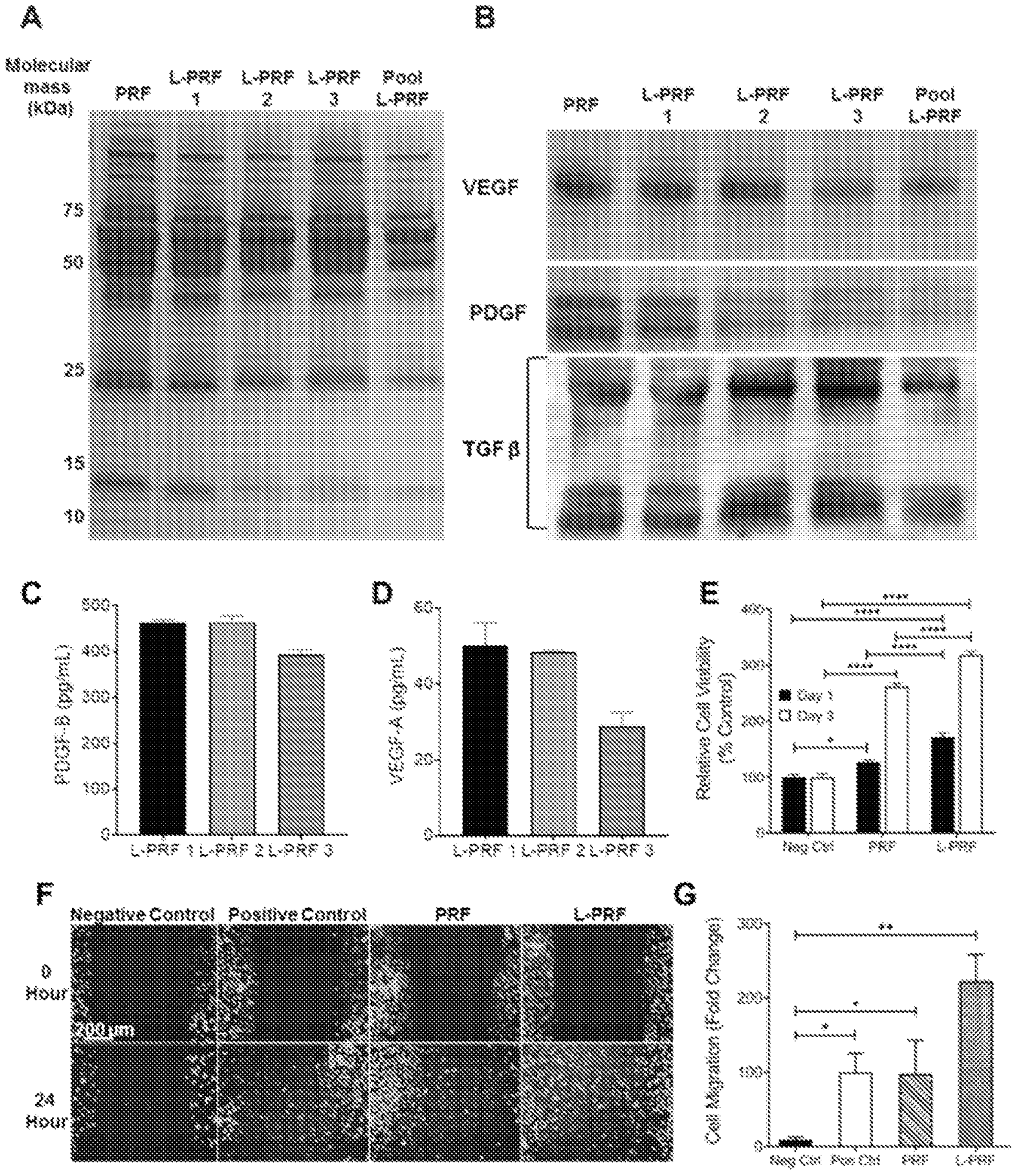
FIGS. 9A-9G. In vitro analysis of PRF and L-PRF.

To make BEMs, a platelet rich fibrin (PRF) fraction from a freshly collected aliquot of pig whole blood was isolated. This straw-colored, gel-like material, which includes polymerized fibrin mesh, growth factors, and platelets, offers several favorable features for an embolic agent such as antibacterial and regenerative properties (Dohan et al., *Oral Surg. Oral Med. Oral Pathol. Oral Radiol. Endod.,* 101:e37 (2006)). PRF was further processed to prepare lyophilized PRF (L-PRF) (FIG. 1 and FIG. 8). In this version, L-PRF could be stored at 4° C. for later use to make a BEM. SDS-PAGE of L-PRF and PRF were similar with no significant evidence of degradation during the lyophilization process (FIG. 9A). Furthermore, preserved integrity of selected growth factors in L-PRF and freshly prepared PRF was demonstrated by immunoblotting and enzyme-linked immunosorbent assay (ELISA) experiments (FIG. 9B to 9D). Some variability was noted in the detection level of VEGF-A; this may represent normal variation in the PRF composition of each pig (FIG. 9D). To demonstrate the biological activity of these growth factors in PRF and L-PRF, cell migration and proliferation assays were performed using L-929 mouse fibroblasts. Both PRF and L-PRF demonstrated significantly enhanced cellular proliferation ($p<0.0001$) and migration (PRF; $p<0.05$, L-PRF; $p<0.01$) (FIG. 9E to 9G), suggesting that L-PRF- and PRF-based BEMs will provide adequate bioactivity, which can promote fibroinflammatory responses following arterial embolization to create a durable occlusion avoiding recanalization.

Figure 2:
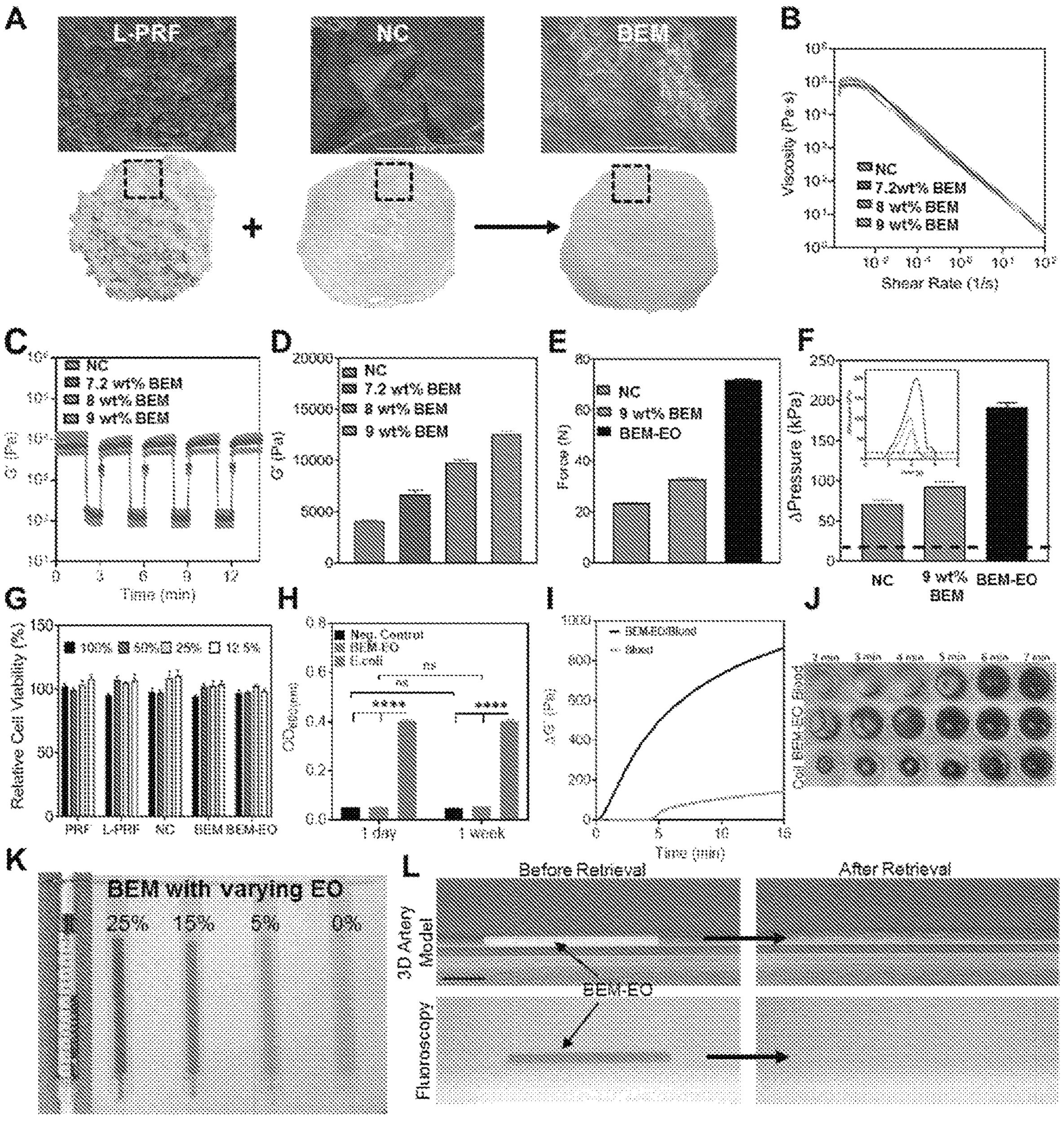
FIGS. 2A-2L. Characterization of BEM.
Figure 10:
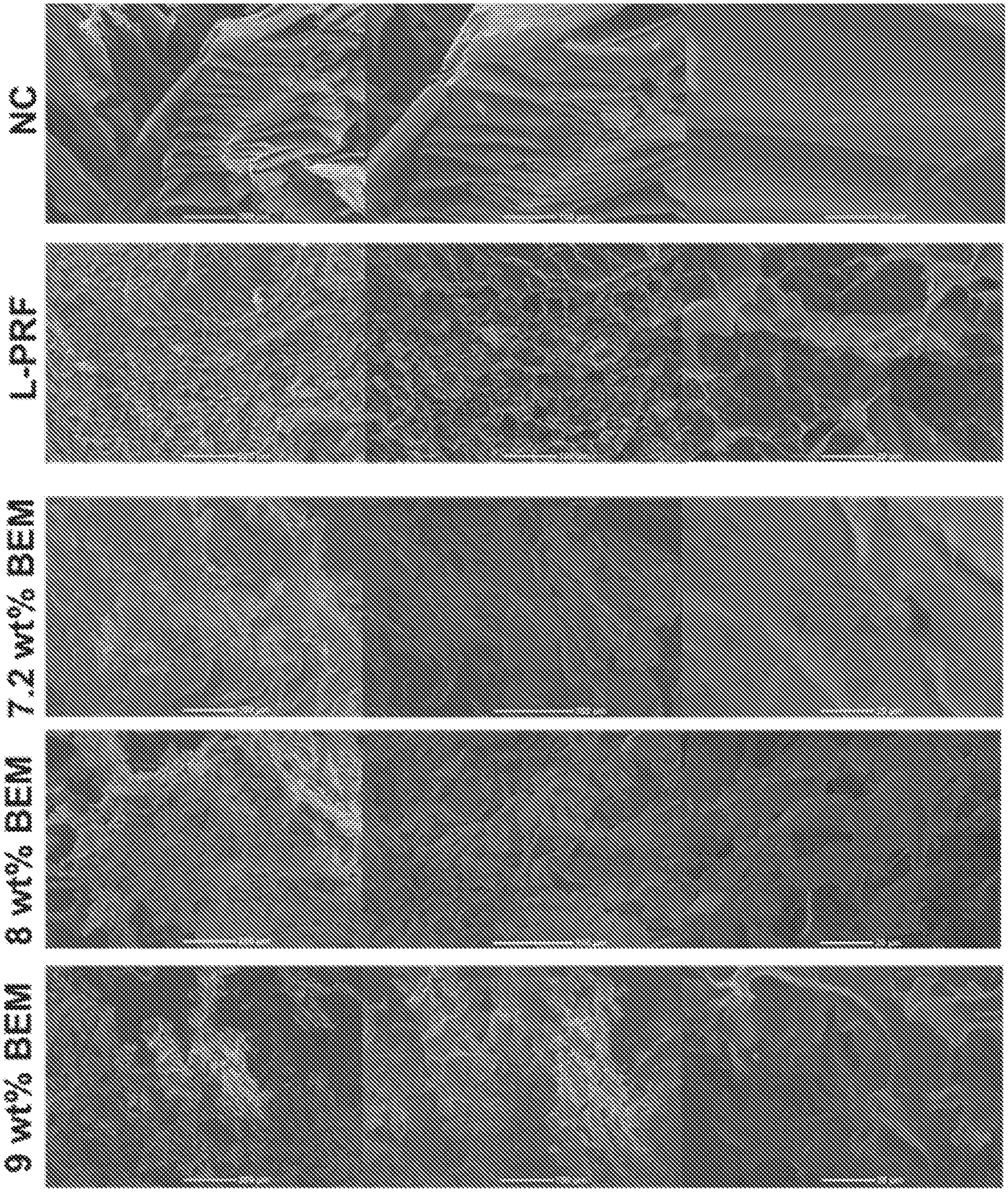
FIG. 10. SEM images of NC, L-PRF, and BEMs. SEM images at different magnification showing a layered structure of NC, honeycomb-like structure of L-PRF, and porous structures of BEMs.

Next, to make L-PRF injectable through clinical catheters, L-PRF was combined with Laponite® nanoclay (NC) to develop a shear-thinning BEM. NC can have antibacterial properties and shear-thinning characteristics that are favorable for injectability (Rawat et al., *Appl. Biochem. Biotechnol.,* 174:936 (2014); Gaharwar et al., *ACS Nano.,* 8:9833 (2014); and Avery et al., *Sci. Transl. Med.,* 8:365ra156 (2016)). NC can include nanosized silicate disks carrying negative charges on the surfaces and positive charges along the rims, which could help to form ionic interactions with PRF proteins (i.e., fibrin). On scanning electron microscopy (SEM), BEMs demonstrated a porous microstructure (FIG. 2A and FIG. 10).

To investigate the interaction between L-PRF and NC, three types of BEM formulations were fabricated with varying amounts of L-PRF (7.2 wt %, 8 wt %, and 9 wt % total solid content) while keeping NC content constant at 6.6 wt % (Table 1). Decreased viscosity upon increased shear rate suggested the shear-thinning ability of NC and BEMs favoring transcatheter injectability in all three formulations (FIG. 2B). In addition, the three types of BEMs demonstrated excellent recoverability under alternating low and high strain cycles, showing the ability of rapid network disruption and reconstitution regardless of oscillation history (FIG. 2C). The addition of L-PRF into NC significantly enhanced its storage modulus, G', which is an indicator of the BEM's stability. In addition, a three-fold increase in modulus was observed in 9 wt % BEMs (12562±475 Pa) when compared to NC gel alone (4097±118 Pa) (FIG. 2D). BEMs (9 wt %) with a high L-PRF content was selected for further studies due to its excellent mechanical properties for catheter delivery and stability.

TABLE 1

Composition of the blood-derived embolic material (BEM). In these formulated BEMs, the percentage of NC was kept constant at 6.6 wt %.

| | L-PRF wt % | Nanoclay (NC) wt % | L-PRF + NC wt % | L-PRF/NC % |
|---|---|---|---|---|
| 7.2 wt % BEM | 0.6 | 6.6 | 7.2 | 9 |
| 8 wt % BEM | 1.4 | 6.6 | 8 | 21 |
| 9 wt % BEM | 2.4 | 6.6 | 9 | 36 |
| 6.6 wt % NC | 0 | 6.6 | 6.6 | 0 |

Figure 11:
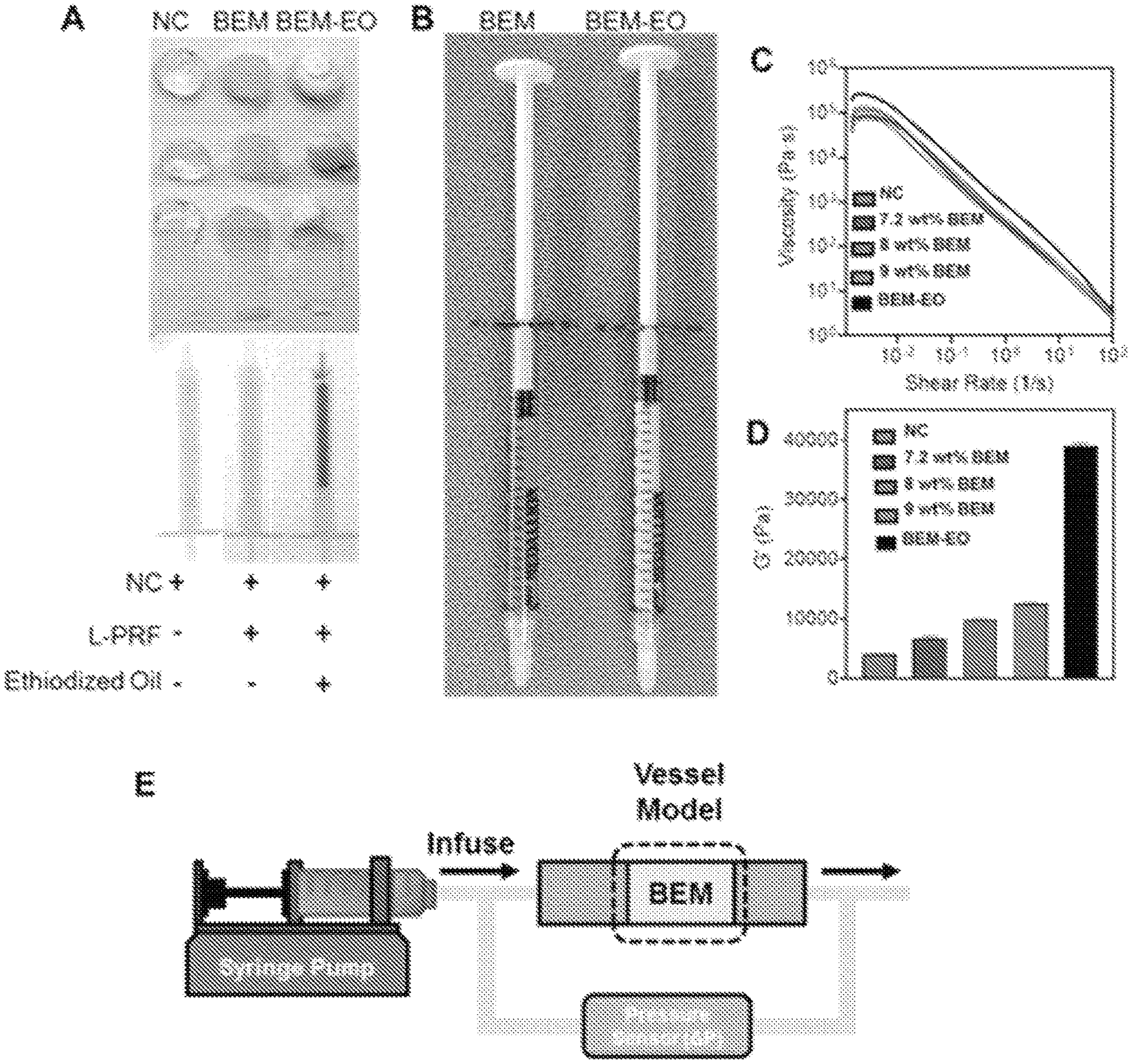
FIGS. 11A-11E. BEM-EO characterization.

To avoid non-target embolization during a procedure, observing the BEM in real-time as it exits the tip of the catheter inside the artery can be carried out. To allow visualization, the BEM was mixed with ethiodized oil, a common contrast agent used in clinical practice with X-ray based imaging modalities, i.e., computed tomography (CT) and fluoroscopy. A commercially available ethiodized oil was mixed with NC and L-PRF to generate a BEM with ethiodized oil (BEM-EO) (FIGS. 11A and 11B). Subsequent rheology testing of BEM-EO demonstrated persistent shear thinning property with excellent G' (39068±575 Pa), which was three times higher compared to BEM alone (FIGS. 11C and 11D).

Next, the physician experience (e.g., the capability to inject by hand is of importance for ease of use, to reduce procedure time and to lower procedure costs) was evaluated. With compression testing, maximum injection forces for NC, BEM, and BEM-EO were measured to be 23±0.3 N, 32±0.6 N, and 71±0.4 N, respectively, indicating the feasibility for hand injection through clinical catheters (FIG. 2E). The enhanced modulus of BEM-EO was further confirmed by measuring the maximum pressure required to displace NC, BEM, or BEM-EO (71±7 kPa, 93±8 kPa, and 192±7 kPa, respectively) in an in vitro vascular occlusion model. BEM-EO demonstrated a displacement pressure approximately 12 times higher than normal systolic pressure, suggesting that when injected in the artery, it will remain in place without migration or fragmentation (FIG. 2F and FIG. 11E).

Figure 12:
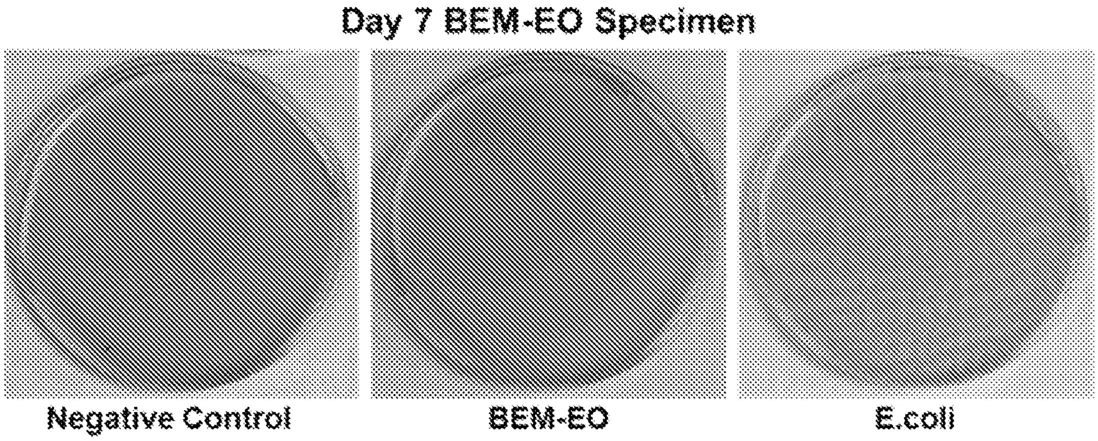
FIG. 12. In vitro evaluation of BEM-EO sterility assay. Gross view images of Mueller Hinton agar plates showing no bacterial growth at day 7 following inoculation with BEM-EO solubilized in LB broth compared to *E. coli* positive control.

Next, cytotoxicity of fresh PRF, L-PRF, NC, BEM, and BEM-EO were evaluated according to ISO 10993-5 guidelines using L-929 cells. No cytotoxicity was observed with any of the tested PRF containing materials, revealing the biocompatibility (FIG. 2G). Radiopaque BEM-EO was selected for use in swine experiments and therefore sterility and hemostatic ability of BEM-EO were investigated. Prior to animal studies, preparation of BEM-EO was mixed with LB broth and incubated at 37° C.; these were shown to be sterile at day 1 and day 7 (FIG. 2H and FIG. 12). Hemostatic activity was tested using rheometry to observe time-dependent modulus changes as BEM-EO came in contact with blood. Rapid increase in modulus was demonstrated when blood came in contact with BEM-EO compared to blood alone (FIG. 2I). Moreover, blood aliquots that were loaded into a 96-well plate were shown to coagulate at 5 minutes, whereas blood with BEM-EO began to coagulate at 3 minutes, which is similar to coils used in clinical practice (FIG. 2J). The concentration of ethiodized oil in BEM was optimized under x-ray fluoroscopy; 25 wt % of ethiodized oil mixed with BEM produced adequate radiopacity to enable tracking under x-ray based imaging modalities (FIG. 2K). Another desired property of an embolic agent is the capability to retrieve them; this would allow rescue of any non-target embolization resulting from accidental delivery. Using the Penumbra Aspiration catheter system (Penumbra, Inc., Alameda, CA), which is an FDA approved device to remove clots that cause stroke, it was explored whether BEM-EO could be retrieved (FIG. 2L). BEM-EO was shown to be retrievable after delivery, which is a unique property that is not possible using the currently FDA approved embolic agents.

Figure 3:
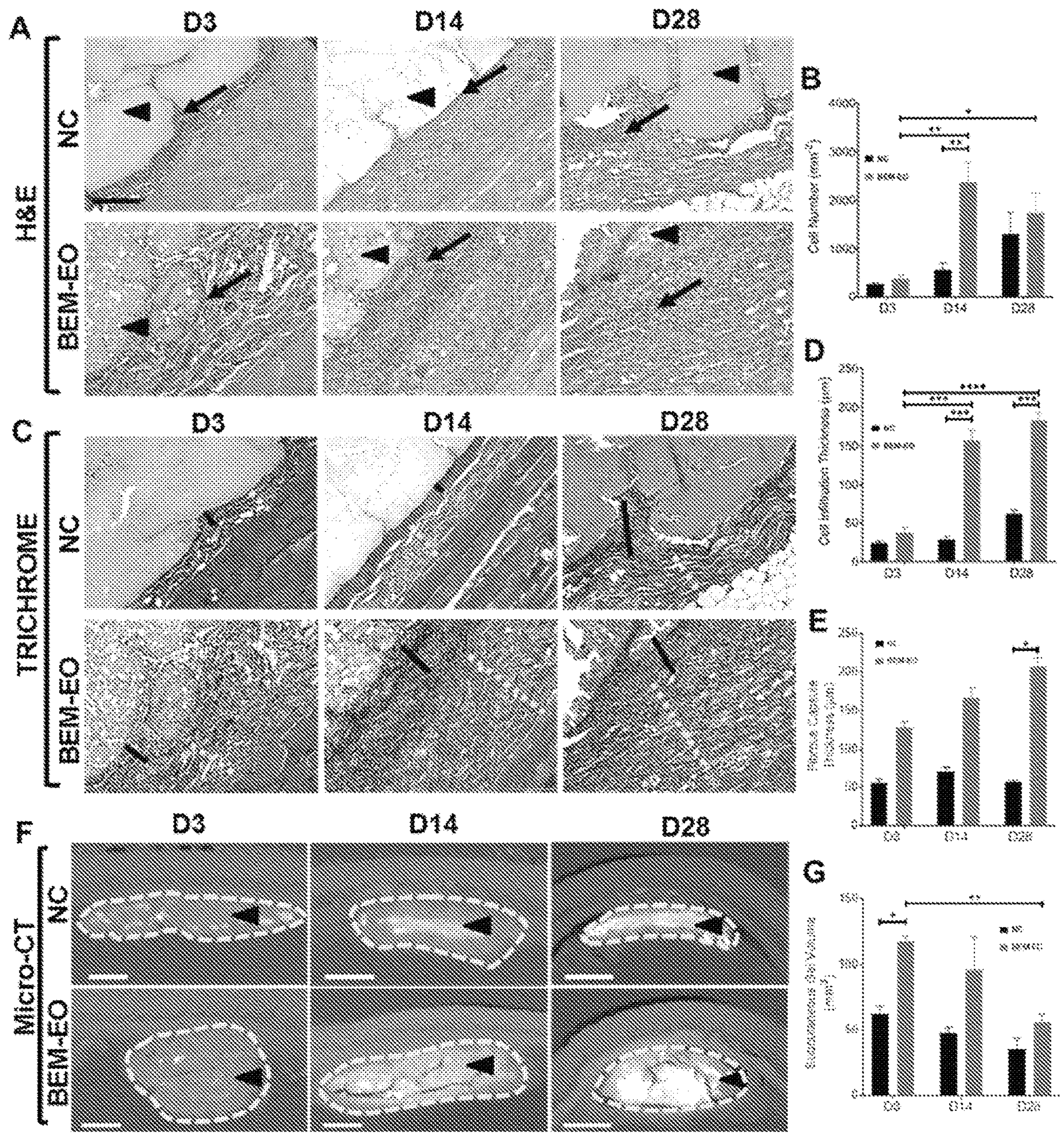
FIGS. 3A-3G. Assessing the histologic response following subcutaneous implantation of NC or BEM-EO in the rats' dorsum.

To further evaluate the biocompatibility and biodegradation profiles of NC, BEM, and BEM-EO, a rat subcutaneous injection model was used (FIG. 13); the injectate and the surrounding tissue at day 3, 14, and 28 post-implantation were explanted. Histological examinations revealed amorphous eosinophilic appearing BEM and BEM-EO in the injection site (FIG. 3, FIG. 14); H&E staining was used for total cell counts, and trichrome staining was used to demonstrate collagen deposition. In the BEM-EO group, significantly higher number of cells were observed at day 14 ($p<0.01$) and day 28 ($p<0.05$) compared to day 3 (FIGS. 3A and 3B, arrows). Higher numbers of cells were also present in BEM-EO compared to NC at day 14 (FIGS. 3A and 3B, arrows). Furthermore, the injectate was surrounded by a layer of cellular infiltration (FIG. 3C, black line) and collagen rich fibrous capsule (FIG. 3C, dotted line). In the day 14 group, both BEM ($p<0.05$) and BEM-EO ($p<0.001$) had significantly thicker layer of cellular infiltration compared to NC group, suggesting that the L-PRF likely had a proliferative effect (FIGS. 3C and 3D, FIGS. 14A and 14C, black line). Day 28 BEM-EO samples also demonstrated a thicker collagen rich fibrotic capsules, representing an increase in collagen deposition around the biomaterial compared to NC (FIGS. 3C and 3E, dotted line). This enhanced fibrosis would be beneficial for stabilizing the injected material in the vessel to achieve durable embolization and prevent recanalization in the long term. The change in the injected material volume was measured from reconstructed micro-CT images of explanted tissues, as shown in FIGS. 3F and 3G; significant volume reduction was observed in BEM ($p<0.05$) and BEM-EO ($p<0.01$) between day 3 and day 28 on micro-CT images (FIGS. 3F and 3G, FIG. 14E), revealing the biodegradability. Analysis of the blood samples from all rats further supported the biocompatibility of NC, BEM, and BEM-EO; complete blood count (CBC) studies showed normal levels of leukocytes, red blood cells, and platelets (Table 2).

TABLE 2

Complete Blood Counts (CBC) of rats that received subcutaneous injections of NC, BEM, and BEM-EO. Blood samples taken from control animals that had no injections and subcutaneously injected animals were compared. All values were within the normal range of rats. (One-way ANOVA, Dunnett's multiple comparisons test, n = 4).

| Parameter [Unit] | Control | D 3 | D 14 | D 28 |
|---|---|---|---|---|
| White Blood Cells ($10^3$ $\mu L^{-1}$) | 10.6 ± 1.8 | 8.2 ± 2.7 | 12.4 ± 2.1 | 11.1 ± 1.8 |
| Lymphocytes ($10^3$ $\mu L^{-1}$) | 8.5 ± 1.3 | 4.9 ± 1.8* | 8.4 ± 1.5 | 7.5 ± 1.5 |
| Monocytes ($10^3$ $\mu L^{-1}$) | 0.4 ± 0.08 | 0.45 ± 0.1 | 0.6 ± 0.08 | 0.5 ± 0.08 |
| Granulocytes ($10^3$ $\mu L^{-1}$) | 1.6 ± 0.5 | 2.8 ± 0.9 | 3.3 ± 0.7** | 3.1 ± 0.2* |
| Red Blood Cell Count ($10^6$ $\mu L^{-1}$) | 6.7 ± 0.3 | 6.7 ± 0.4 | 7.1 ± 0.4 | 7.3 ± 0.3 |
| HCT (%) | 36 ± 1.3 | 34 ± 1.7 | 34.6 ± 2.35 | 36.5 ± 0.5 |
| Platelet ($10^3$ $\mu L^{-1}$) | 316 ± 36 | 306 ± 65.2 | 205 ± 31.9 | 276 ± 95 |

*$p \leq 0.05$,
**$p \leq 0.01$.
Data are represented as average ± S.D.

Figure 15:
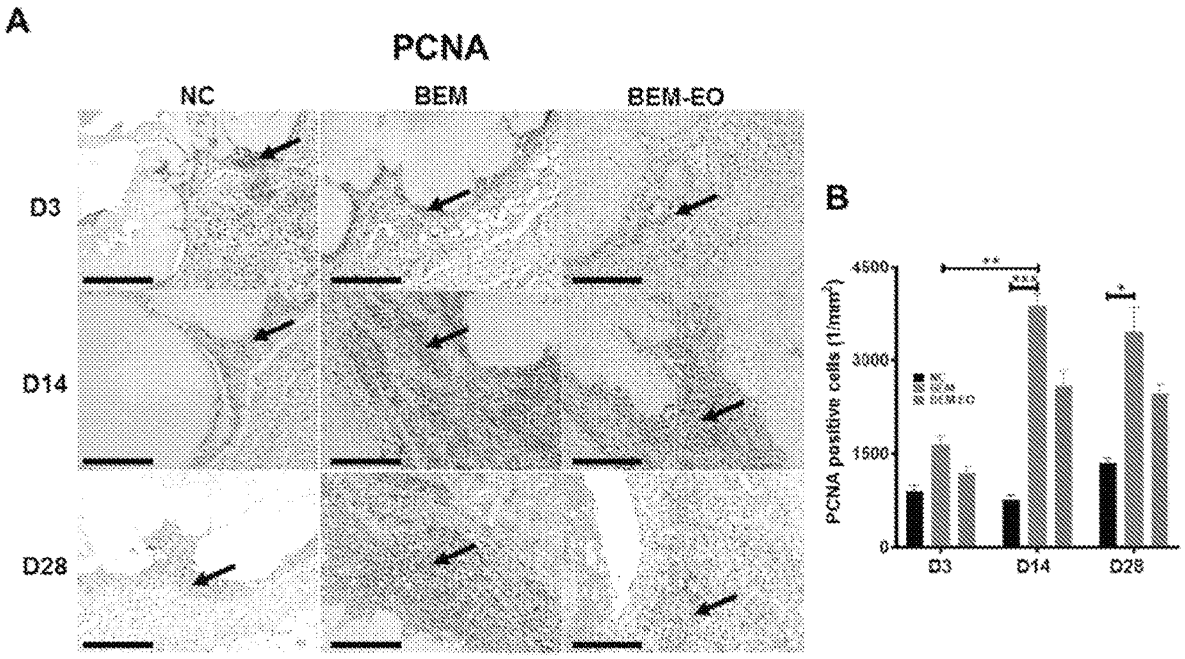
FIGS. 15A-15D. Assessing cellular proliferation and angiogenesis in rat subcutaneous tissue following biomaterial implantation.
Figure 15:
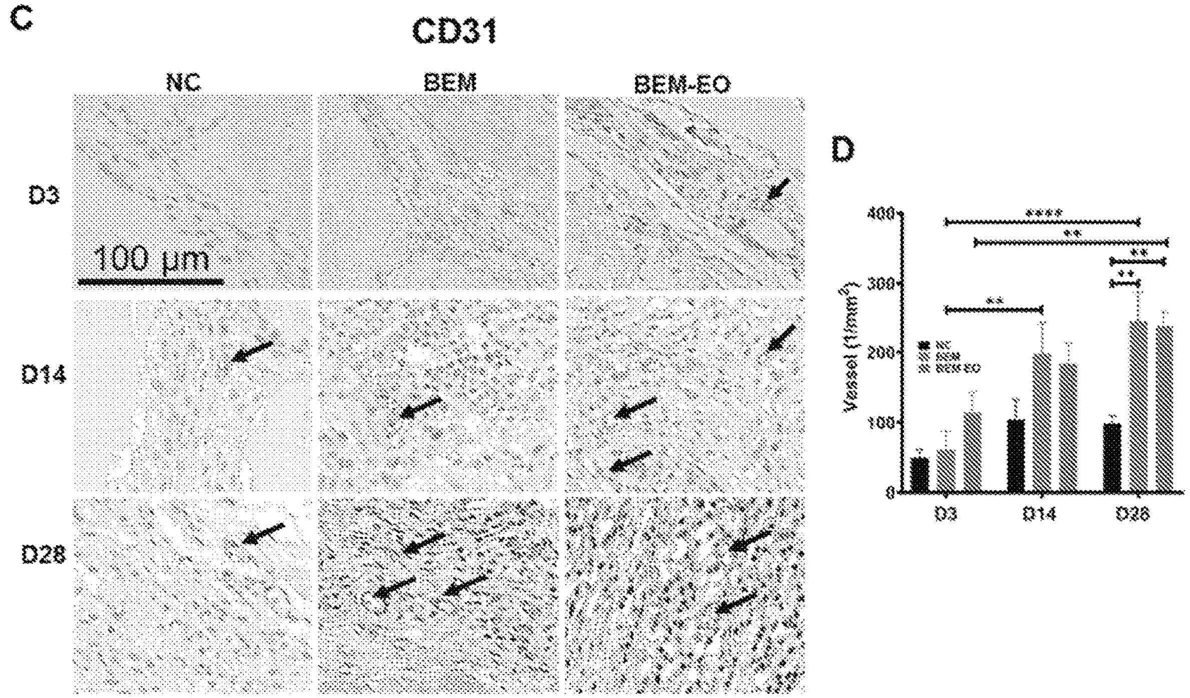

Angiogenesis and cell proliferation are essential for soft tissue healing. Proliferating cell nuclear antigen (PCNA) immunostaining in the rat subcutaneous injection model showed a significantly higher number of proliferating cells in the BEM group compared to NC at day 14 ($p<0.001$) and day 28 ($p<0.05$) (FIGS. 15A and 15B). Angiogenesis at the tissue-injectate interface was also evaluated using CD31 immunostaining showing a significantly higher number of vessels formed in the BEM and BEM-EO samples at day 28 compared to NC ($p<0.01$) (FIGS. 15C and 15D). These findings are also consistent with in vitro cell proliferation and migration assays suggesting that BEM-EO can incite a regenerative response that promotes biodegradation and fibrosis, which are properties involved in achieving a durable occlusion in the arterial lumen.

Figure 4:
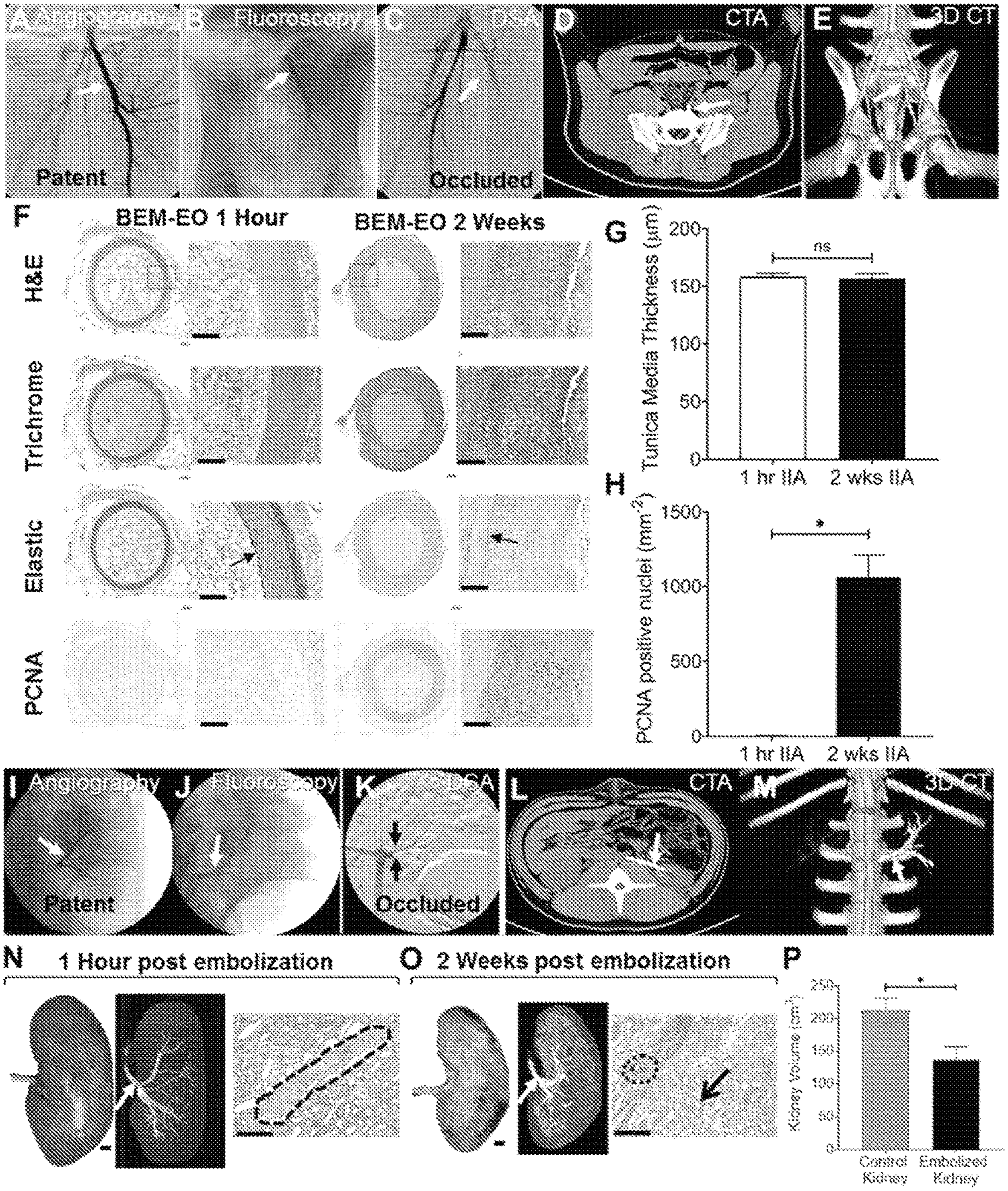
FIGS. 4A-4P. Catheter-directed embolization of iliac and renal arteries using BEM-EO in swine.
(FIG. 4B) Single-shot x-ray fluoroscopic image of BEM-EO in the IIA after embolization (white arrow).
(FIG. 4C) Post-embolization DSA confirming occlusion of the IIA (white arrows).
(FIG. 4D) Axial computed tomography (CT) image of an embolized IIA; white arrow shows BEM-EO.
(FIG. 4E) 3D reconstructed CTA image of distal aorta and iliac arteries; embolized iliac artery with the bright BEM-EO casting the IIA (white arrow).
(FIG. 4F) Micrographs of stained histologic cross sections of IIA occluded with BEM-EO at 1 hour and 2 weeks following embolization; 2-week survival group, extensive concentric fibroinflammatory reaction with disrupted elastin in the arterial wall (black arrows).
(FIG. 4G) Morphometric analysis of arterial wall medial thickness assessed in elastic stained histologic sections.
(FIG. 4H) Summary of PCNA positive cell counts shows significant increase at 2 weeks following embolization.
(FIG. 4I) Pre-embolization angiography showing patent renal artery segmental branches (arrow).
(FIG. 4J) Fluoroscopic image showing BEM-EO in renal artery after embolization (arrow).
(FIG. 4K) Post-embolization digital subtraction angiography showing complete occlusion of renal artery with BEM-EO (between arrows).
(FIG. 4L and FIG. 4M) Axial CT image and 3D rendered CT image of embolized kidney showing visible BEM-EO inside the artery with no imaging artifact (white arrow).
(FIG. 4N and FIG. 4O) Micro-CT, gross view, and histology images of pig kidneys at 1 hour and 2 weeks following embolization showing BEM-EO in renal artery on micro-CT (white arrow); stained histologic images shows an arterial branch filled with BEM-EO at 1 hour and 2 weeks post embolization (black outlined area) and necrotic tubular cells are observed at two weeks after embolization (black arrow).
Figure 16:
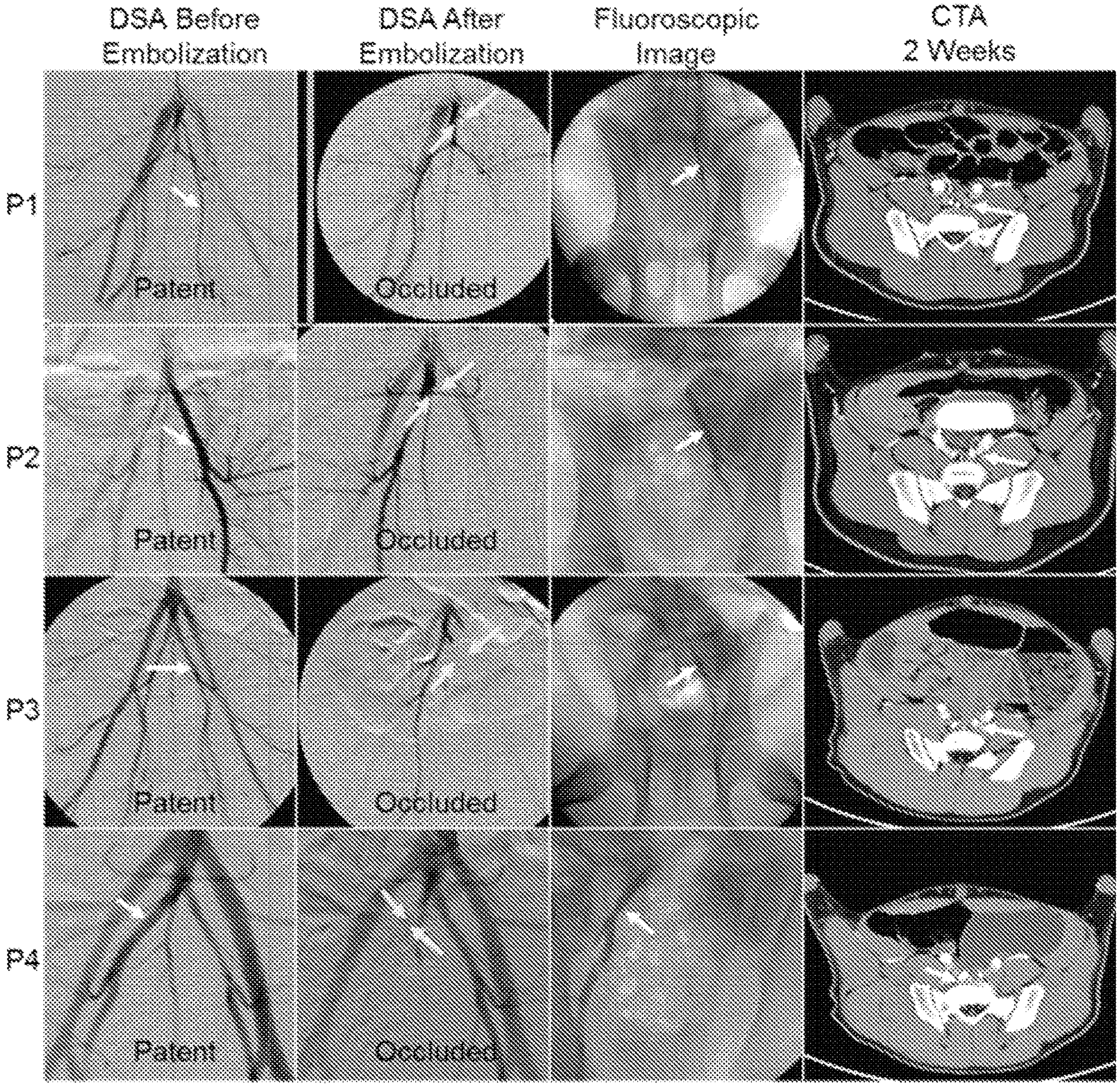
FIG. 16. Swine internal iliac artery embolization with BEM-EO. Fluoroscopic images showing internal iliac artery at baseline and following embolization with BEM-EO in four pigs. Before embolization, patency of iliac arteries (white arrows) is demonstrated by DSAs. After embolization, DSAs show no blood flow in the embolized iliac arteries (between the two arrows). BEM-EO is easily detectable following embolization of single-shot fluoroscopic images (white arrows). Panel of computed tomography angiography images showing BEM-EO casting the IIA at two weeks following embolization (white arrows).

Next, a pre-clinical model of arterial embolization in swine was used to test the capability of BEM-EO to achieve embolization without recanalization in a state of anticoagulation (i.e., Activated Coagulation Time (ACT)>300 seconds). Following intra-arterial access into the carotid artery, a clinical catheter was advanced to the distal aorta, and digital subtraction angiography (DSA) was performed revealing the normal arterial anatomy of the pig iliac artery (FIG. 4A). Under real-time fluoroscopy, the catheter tip was brought to the mid-portion of the iliac artery, and syringes with BEM-EO were connected to the catheter via a Luer lock and injected into the internal iliac artery (IIA) over 15-20 seconds. BEM-EO demonstrated excellent visibility during injection (FIG. 4B). Immediately after embolization, DSA from the distal aorta was again performed showing instant occlusion of the iliac artery; no evidence for fragmentation, distal migration, or non-target embolization was observed (FIG. 4C). In contrast to metallic coils, these anticoagulated pigs demonstrated that thrombosis is not necessary for BEM-EO to achieve occlusion. Following embolization, 4 pigs were sacrificed after 1 hour, and another 4 pigs were survived for two weeks and sacrificed following whole-body CT angiogram (CTA) imaging. After 14 days post-embolization, CTAs showed that BEM-EO was still visible in IIA without any artifact, fragmentation, displacement or migration, or BEM-EO recanalization (FIGS. 4D and 4E). Fluoroscopic images of all animals and CTA studies of day 14 pigs consistently showed successful embolization (FIG. 16).

Figure 17:
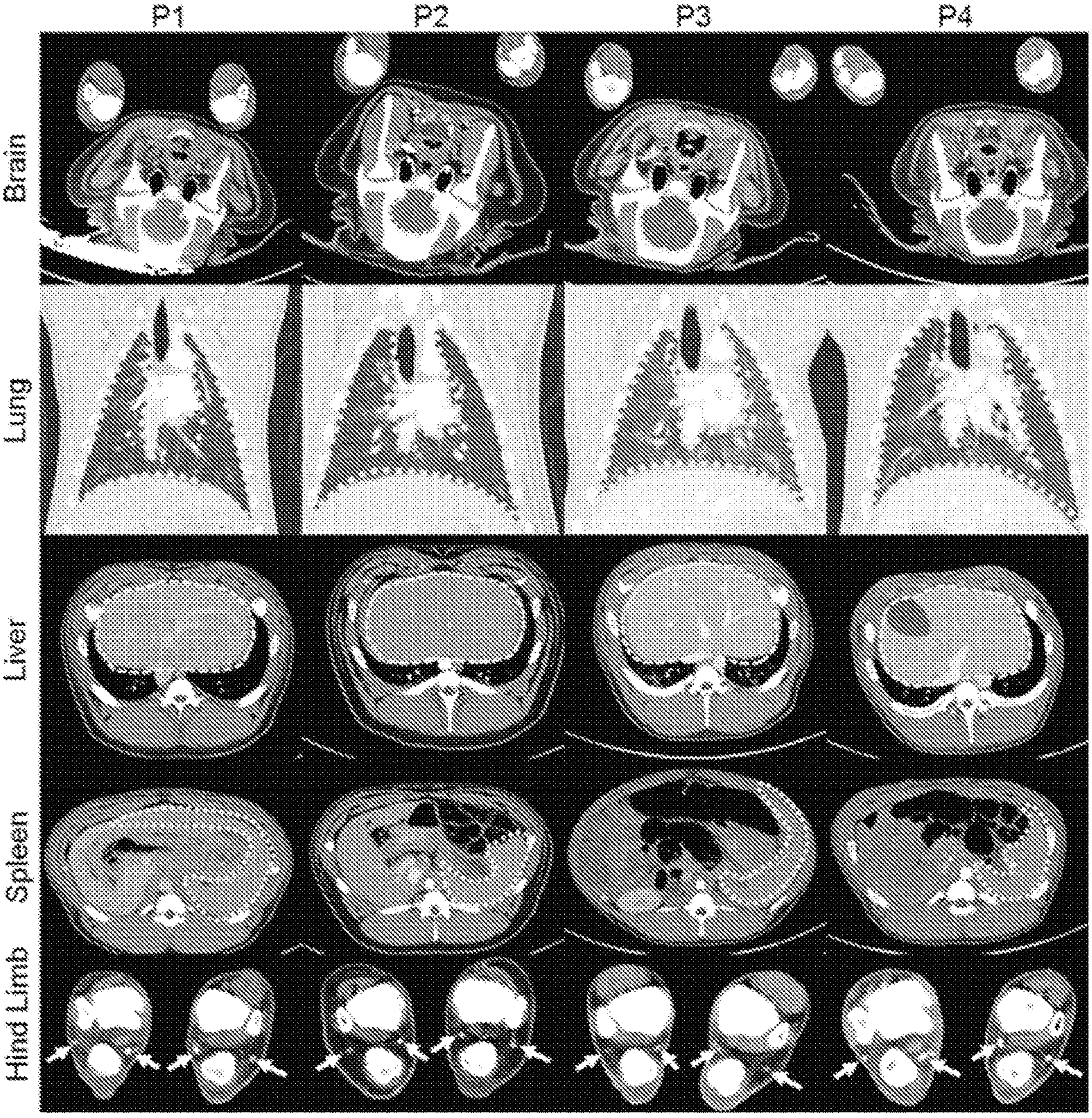
FIG. 17. Whole body CT imaging at two weeks following embolization in pigs. A panel of CT scans of the brain, liver, spleen and hind limb and lungs of four pigs are shown (dashed lines). No abnormalities were found in all tissues. White arrows indicate normal run-off in the arteries of both hind limbs.
Figure 18:
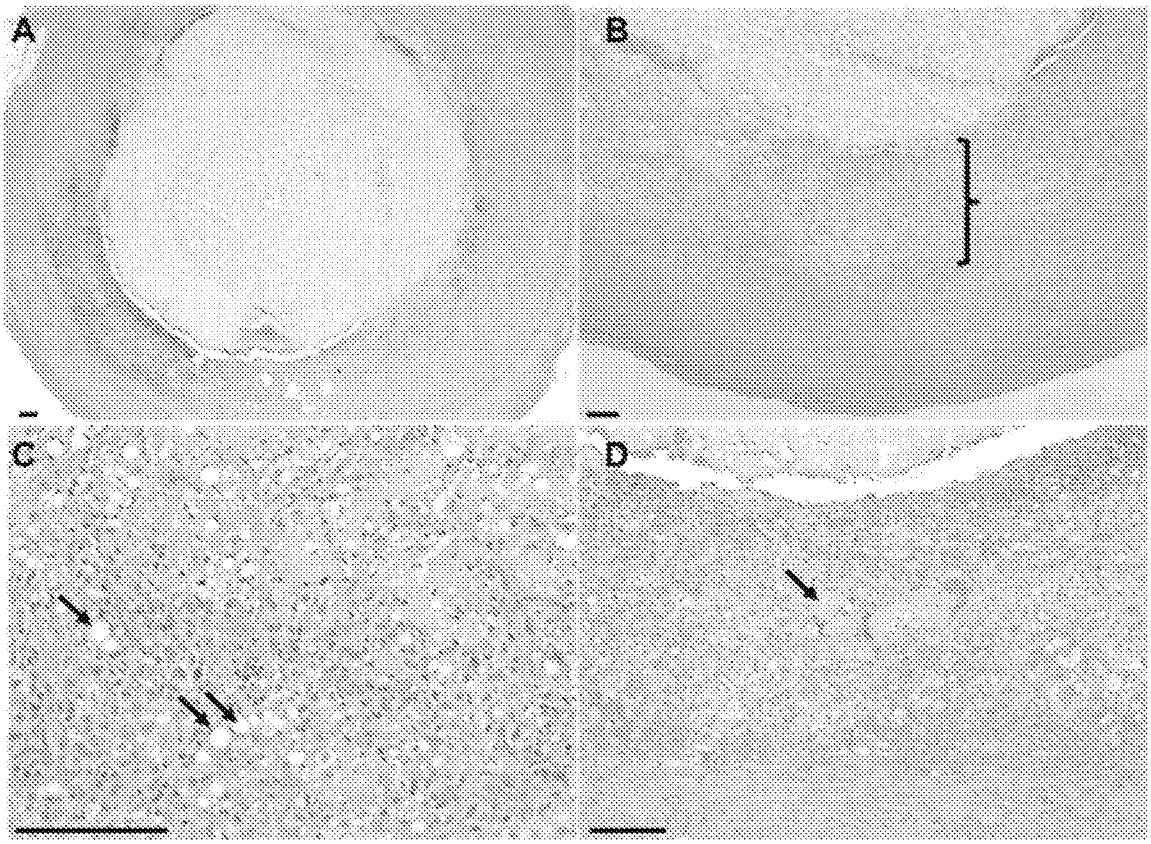
FIGS. 18A-18D. Histologic evaluation of internal iliac artery (IIA) at two weeks following embolization with BEM-EO.

Furthermore, on review of the CT scans by a board certified radiologist, all studies demonstrated normal flow to the distal hindlimb without any evidence of non-target embolization. In addition, there was no evidence for lymphadenopathy or any abnormal findings in the brain, lungs, liver, or the spleen (FIG. 17). Just prior to sacrifice, blood samples were collected, and during necropsy, the embolized arteries were harvested and subjected to high resolution micro-CT imaging and histology. Histologic evaluation of the harvested IIAs was performed by a certified pathologist. In the one-hour non-survival group, flocculent amorphous material was seen casting the arterial lumen with minimal tissue reaction (FIG. 4F). In the two weeks survival group, the arterial lumen was completely occluded by BEM-EO with extensive concentric fibroinflammatory reaction rich in macrophages, myofibroblasts, and fibrin, resembling granulation tissue (FIG. 4F). Scattered multinucleated giant cells and macrophages with fat droplets were also observed (FIG. 18). While the thickness of the tunica media layer between the two groups was similar ($p>0.05$), the two-week survival group showed fibrosis and disruption of the elastic fibers of the intima and media layers (FIG. 4F (black arrows) and 4G). Immunostaining for PCNA, however, showed a significant increase in cell proliferation ($p<0.05$) in the embolized IIAs at 2 weeks compared to the non-survival group (FIGS. 4F and 4H).

Figure 19:
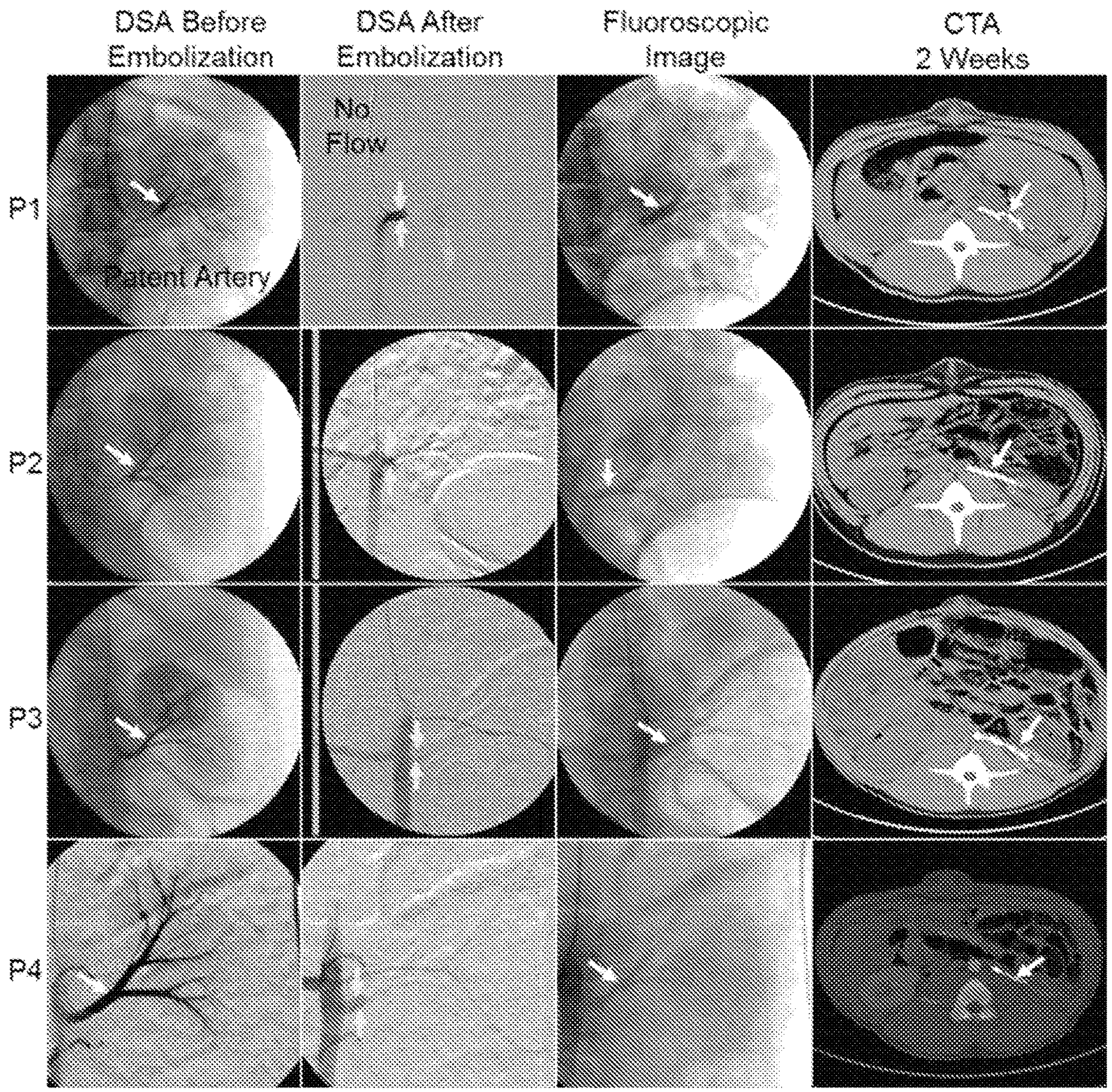
FIG. 19. Swine renal artery embolization with BEM-EO. A panel of fluoroscopic images showing renal artery at baseline (before embolization) and complete occlusion after embolization with BEM-EO in four pigs. Computed tomography angiography images obtained at two weeks after renal artery embolization with BEM-EO showing persistent occlusion in four pigs (white arrow). After embolization, DSA shows absence of flow in the embolized renal artery and in the kidney; on single-shot fluoroscopic image and on axial CTA, BEM-EO is easily detectable (white arrows).
Figure 20:
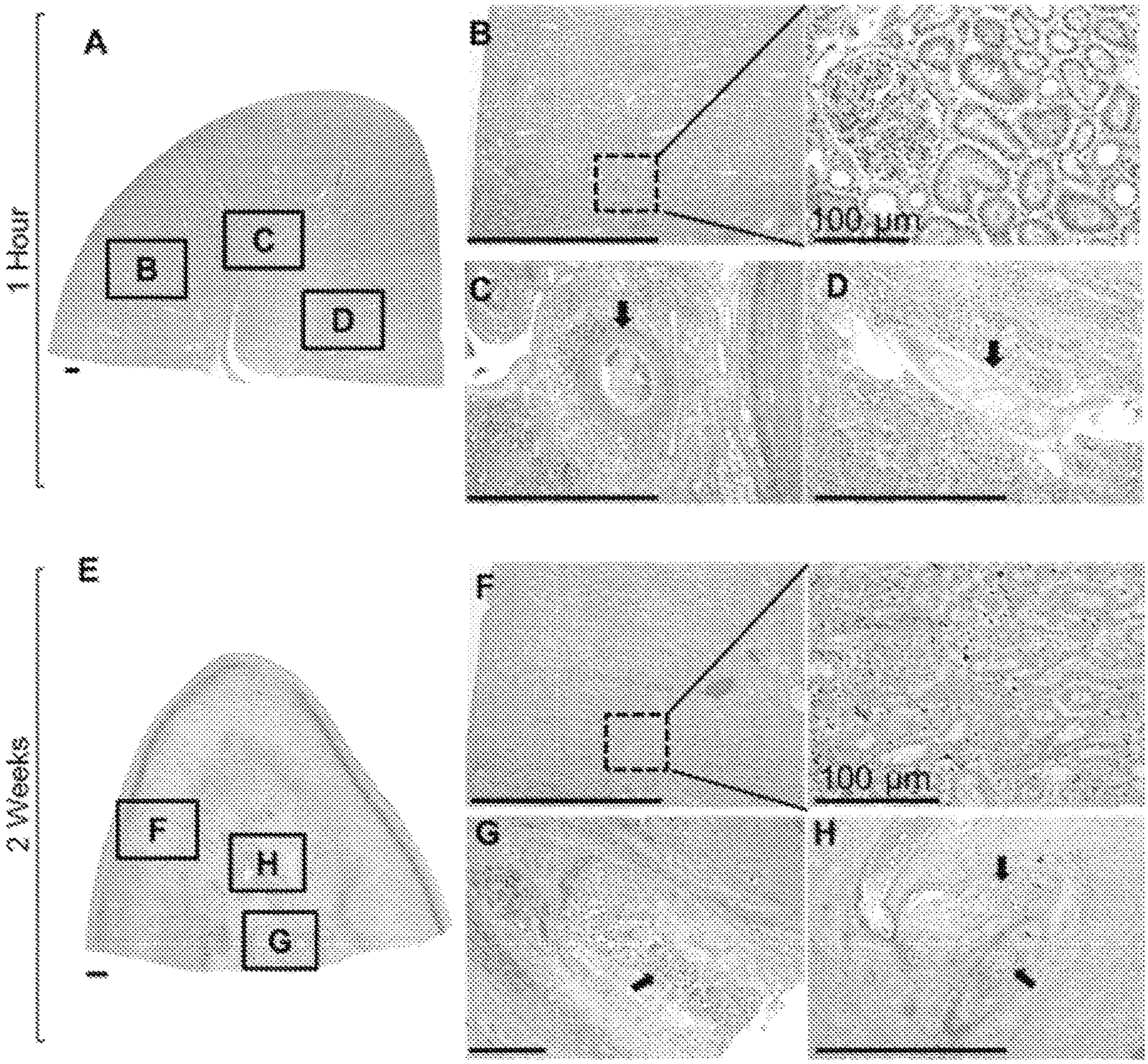
FIGS. 20A-20H. Histology images of BEM-EO embolized renal parenchyma.

In the pelvis, there is often extensive redundancy in the vascular flow that helps bypass an occlusion. IV contrast CTA images in the 2-week survival group showed contrast opacification distal to BEM-EO; while this almost certainly represents collateral blood flow, recanalization could not be entirely excluded. To assess for recanalization, an end organ artery without arterial redundancy was embolized. In this case, the main renal artery of the kidney was selected for BEM-EO embolization. A total of 8 pigs had the main renal artery embolized under fluoroscopy in a state of anticoagulation during the procedure; 4 were sacrificed at 1 hour, and another 4 were sacrificed after two weeks following embolization. FIG. 4I shows normal renal angiography. Subsequently, BEM-EO was injected into the renal artery through a 5F clinical catheter during real-time fluoroscopy (FIG. 4J). Following embolization, DSA images showed the absence of flow through the embolized renal artery (FIG. 4K). Just prior to sacrifice in the survival group, CTA was performed again showing complete occlusion of the renal artery without any recanalization or imaging artifact (FIGS. 4L and 4M). Renal artery embolization with BEM-EO was successfully achieved in all animals (FIG. 19). Concordantly, CTA studies showed that there was no evidence for contrast enhancement of the embolized kidneys at two weeks demonstrating unequivocally that recanalization was not observed (FIG. 19). Both embolized and contralateral normal kidneys were harvested and evaluated by high resolution micro-CT imaging and by histology. Micro-CT images demonstrated complete filling of the renal artery with BEM-EO (FIGS. 4N and 4O). On histology, the kidney parenchyma in the non-survival group was still viable; BEM-EO was seen in the hilar and segmental arteries (FIG. 20A to 20D). In the 2-week survival group, uniform ischemia in the renal parenchyma with a fibroinflammatory reaction in the occluded hilar and segmental arteries were again noted (FIG. 20E to 20H). These changes were consistent with significant loss of volume ($p<0.05$) in the embolized kidneys at two weeks compared to the non-treated kidneys, indicating successful embolization of the renal artery (FIG. 4P).

To assess for any systemic side effects of BEM-EO embolization, blood samples were collected before and after embolization in each pig. Complete blood count (CBC), basic metabolic panel (BMP), liver function tests (LFTs), and cytokines levels using a protein array showed values that were unremarkable and within normal range (Table 3). At two weeks, an increase in creatinine level was observed in the cohort that received renal artery embolization indicating an expected functional outcome of successful embolization with BEM-EO.

TABLE 3

Summary of complete count, blood chemistry values, and cytokines levels blood samples obtained at baseline before procedure and at 2 weeks following embolization. All values show pig blood samples before embolization and prior to euthanasia in the two-week survival group are shown (Paired t-test, n = 4). Data are represented as average ± S.D. All values were within the normal range.

| Parameter (Unit) | Before Surgery | 2 WEEKS | P value |
|---|---|---|---|
| White Blood Cells ($10^3$ $\mu L^{-1}$) | 14.1 ± 2.5 | 15.9 ± 3.1 | ns |
| Lymphocytes ($10^3$ $\mu L^{-1}$) | 7.7 ± 0.9 | 8.8 ± 1.8 | ns |
| Monocytes ($10^3$ $\mu L^{-1}$) | 1.02 ± 0.2 | 1.35 ± 0.4 | ns |
| Granulocytes ($10^3$ $\mu L^{-1}$) | 5.3 ± 2.5 | 5.6 ± 1.4 | ns |
| Hematocrit (%) | 23.3 ± 1.8 | 27 ± 1.7 | 0.04 |
| Red Blood Cell Count ($10^6$ $\mu L^{-1}$) | 5.2 ± 0.5 | 6.21 ± 0.5 | 0.02 |
| Platelet ($10^3$ $\mu L^{-1}$) | 319 ± 46 | 428 ± 96 | 0.02 |
| Total Protein (g $dL^{-1}$) | 5.2 ± 0.4 | 6.42 ± 0.2 | 0.01 |
| Alkaline Phosphatase (U $L^{-1}$) | 190 ± 52 | 190 ± 48 | ns |
| Glucose (GLU) (mg $dL^{-1}$) | 103 ± 21 | 99 ± 8.4 | ns |
| Alanine Aminotransferase (ALT) (U $L^{-1}$) | 38 ± 4.4 | 38.5 ± 2.8 | ns |
| Creatinine (CRE) (mg $dL^{-1}$) | 1.22 ± 0.09 | 1.6 ± 0.14 | 0.04 |
| Blood Urea Nitrogen (BUN) (mg $dL^{-1}$) | 10.2 ± 2.4 | 14 ± 5.1 | ns |
| INF-γ (pg $ml^{-1}$) | 3143 ± 4249 | 1938 ± 3382 | ns |
| IL-1 alpha (pg $ml^{-1}$) | 476 ± 321 | 880 ± 960 | ns |
| IL-6 (pg $ml^{-1}$) | 184 ± 171 | 230 ± 203 | ns |
| IL-10 (pg $ml^{-1}$) | 1385 ± 1198 | 2104 ± 2281 | ns |
| IL-12 (pg $ml^{-1}$) | 945 ± 288 | 1691 ± 1110 | ns |

Figure 5:
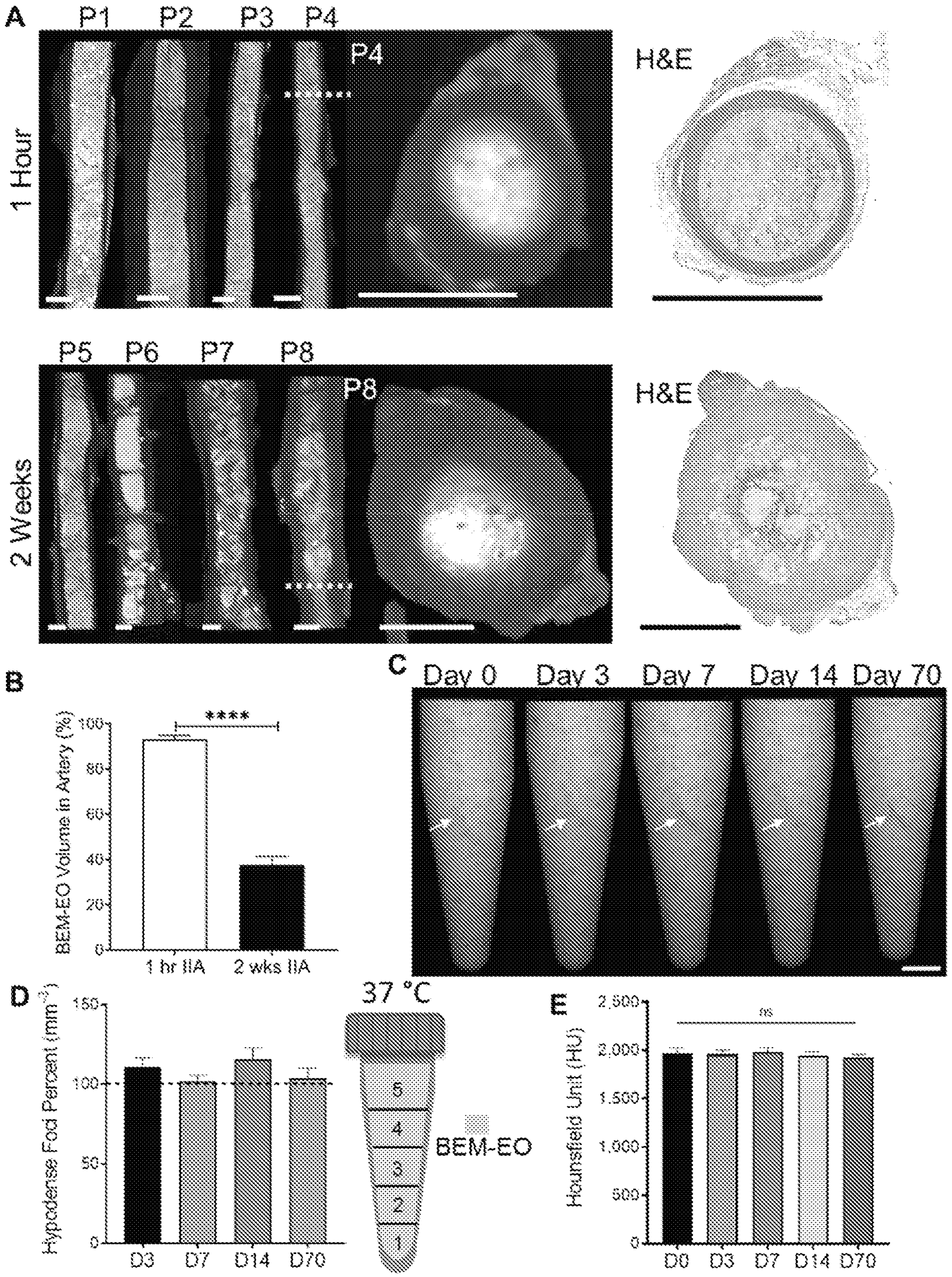
FIGS. 5A-5E. Assessing time-dependent structural changes of BEM-EO using micro-CT.

On further micro-CT analysis of the embolized iliac arterial segments, the one-hour non-survival group showed complete filling of the arterial lumen with BEM-EO on both coronal and axial images; the corresponding H&E images showed uniform filling of the arterial lumen (FIG. 5A). The two-week survival group, however, showed a more heterogeneous appearance on coronal views suggesting that degraded BEM-EO over time had been replaced by fibrotic tissue. Axial CT image and the corresponding H&E image show the characteristic concentric fibroinflammatory response to BEM-EO (FIG. 5A). To determine the degradation profile of BEM-EO over two weeks in the survival group, extensive image analysis was performed to segment the BEM-EO inside the artery from the surrounding connective tissue. These data revealed that more than 63% of the BEM-EO had biodegraded at two weeks (FIG. 5B). To assess stability of the BEM-EO composition, samples were stored in a tube at 37° C. and serially imaged at high resolution using micro-CT at day 0, 3, 7, 14, and 70 (FIG. 5C). Extensive image analysis of these tubes was performed including counting of hypodense foci within the micro-CT images and Hounsfield unit measurements throughout the tube. These data demonstrated no significant differences between the tubes over time, suggesting that BEM-EO is stable and that phase separation of its components did not occur (FIGS. 5D and 5E).

Figure 6:
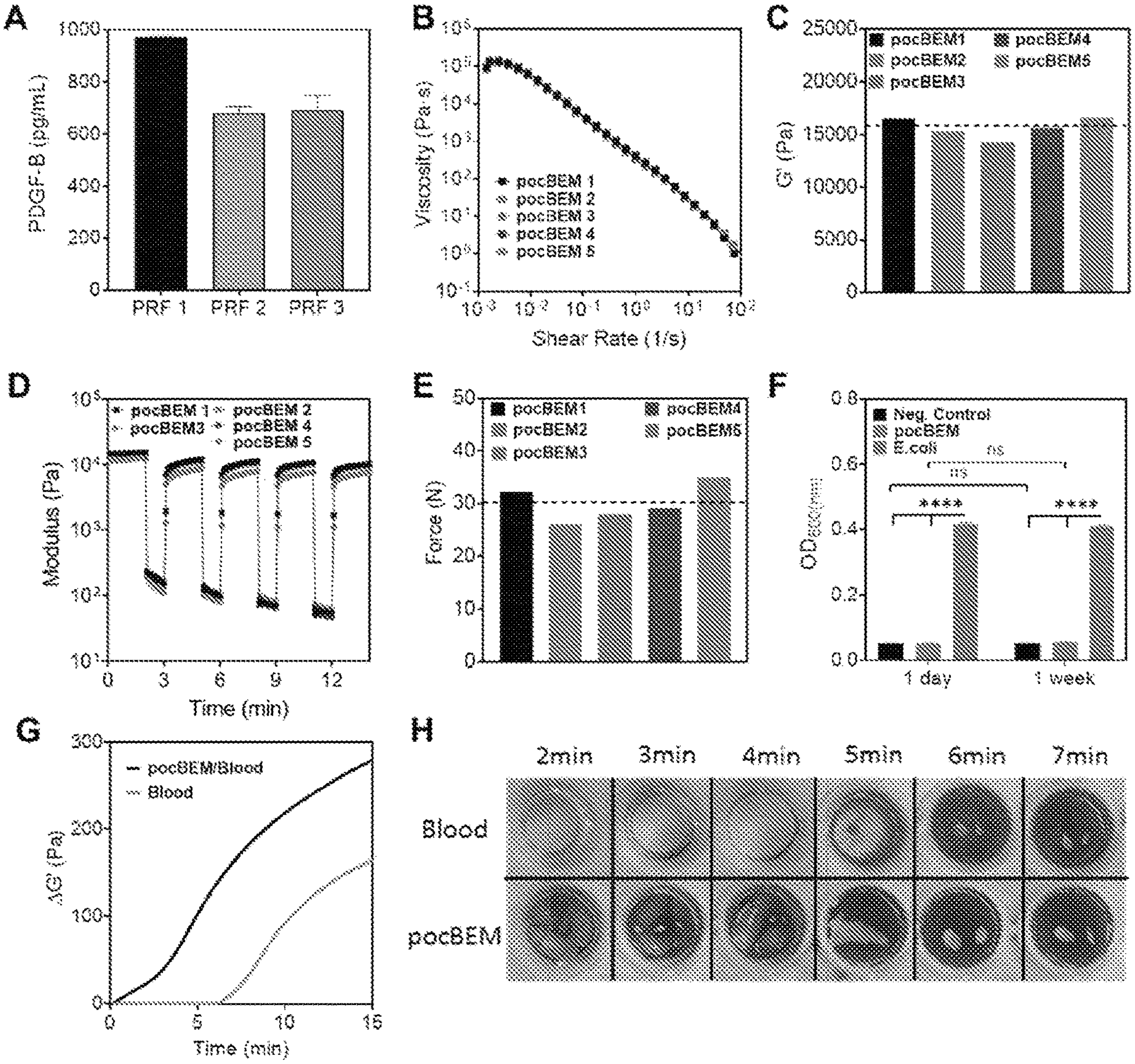
FIGS. 6A-6H. Fabrication and characterization of point of care blood-derived embolic material (pocBEM).
Figure 21:
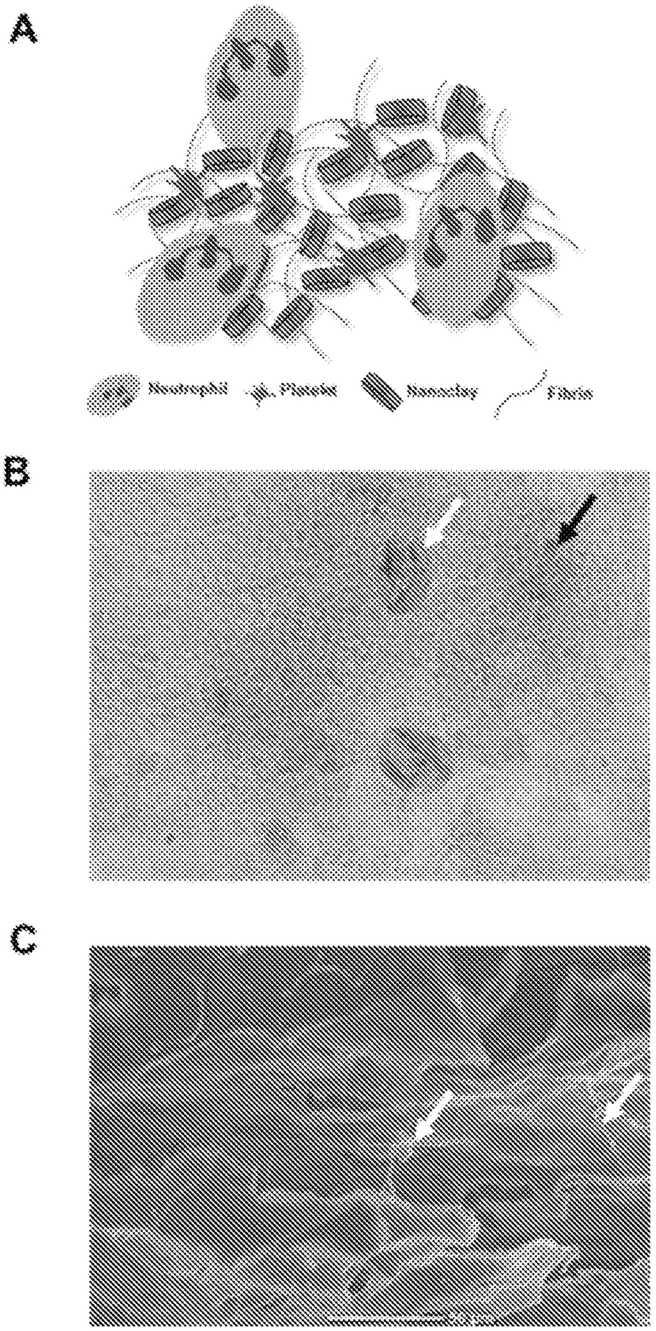
FIGS. 21A-21C. Microstructure of pocBEM.

Next, a version of BEM-EO that can be prepared at point-of-care for urgent or emergent embolization procedures was introduced. Whole blood from the same pig was centrifuged for 3 minutes at 700 rpm to produce a liquid form of PRF that is also rich in growth factors, cells, and proteins (FIG. 6A). This liquid version of PRF was immediately mixed with NC and ethiodized oil to produce the point-of-care version of a BEM, namely pocBEM. The process of preparing ready-to-use pocBEM syringes from blood collection to loading took 26±0.7 minutes (n=5). pocBEMs that were prepared from different pigs (n=5) were similar in viscosity profiles showing consistent shear thinning properties (FIG. 6B). pocBEM also revealed excellent modulus (15685±434 Pa) and recoverability, which are involved in stability of the embolic material to prevent migration or fragmentation inside the artery (FIGS. 6C and 6D). The maximum injection force required to inject pocBEM through a 5 French clinical catheter was measured to be 30±1.5 N (n=5), indicating the feasibility for hand injection (FIG. 6E). In addition, preparation process of pocBEMs was shown to be sterile, without bacterial growth for 1 week (FIG. 6F). Moreover, hemostatic ability of pocBEM was tested. Compared to blood alone, blood in contact with pocBEM coagulated faster, which was also supported by rheological studies (FIGS. 6G and 6H). Lastly, SEM images and H&E staining of pocBEM revealed the presence of fibrin bundles and platelets in pocBEM (FIG. 21).

Figure 7:
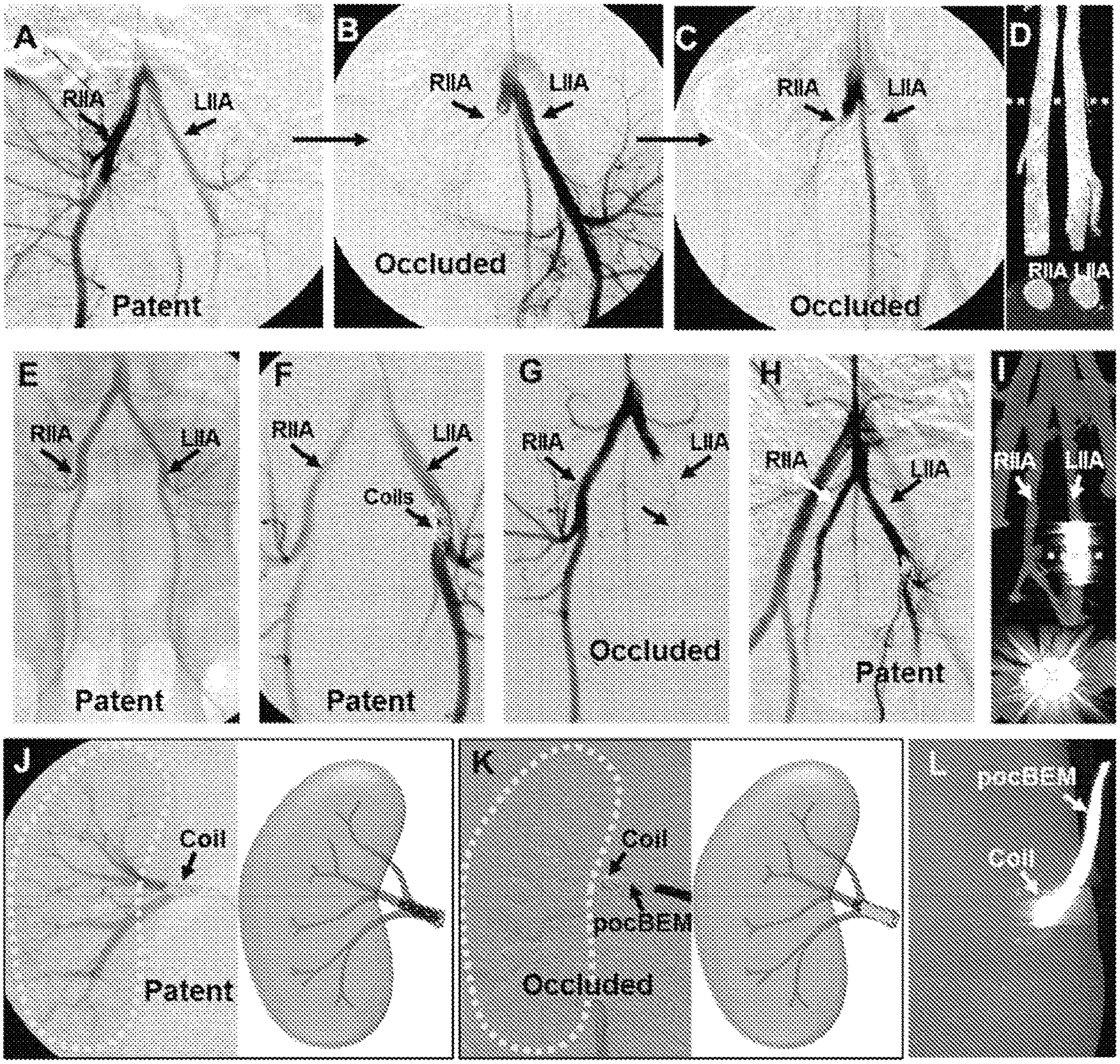
FIGS. 7A-7L. Transcatheter arterial embolization, retrieval, and rescue of failed embolization with coils using pocBEM in swine.
Figure 22:
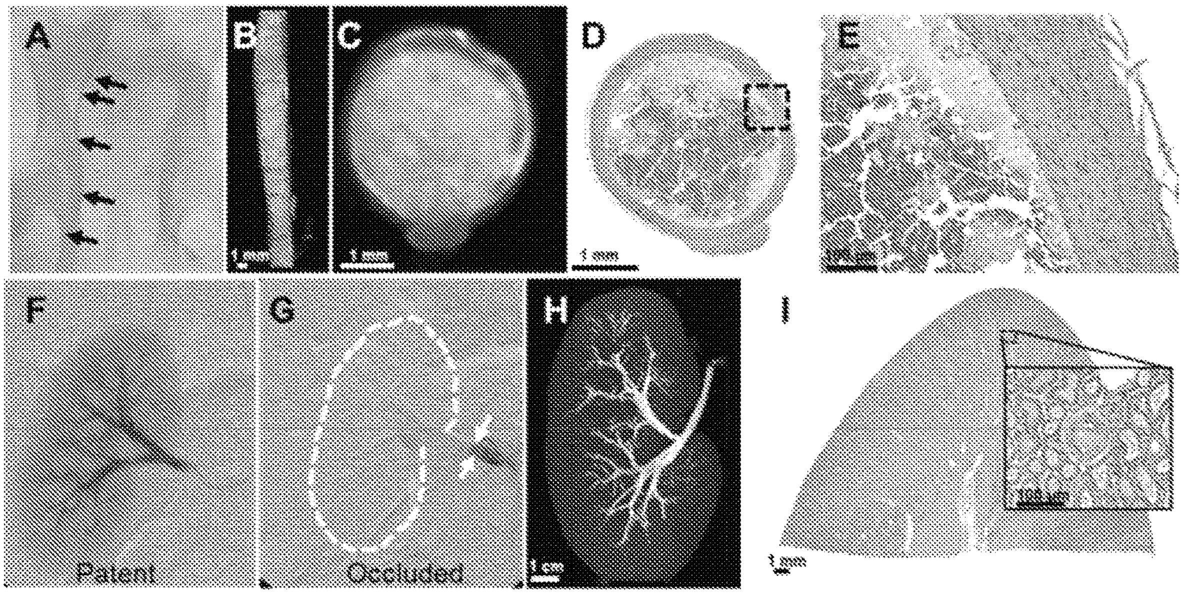
FIGS. 22A-22I. Micro-CT and histology of pocBEM occluded iliac and renal arteries at 1 hour-post embolization.

Following preparation, pocBEM was packed into syringes and injected into the same pig. Iliac arteries of eight pigs and renal arteries of four pigs were successfully embolized using pocBEM. During embolization, pocBEM was visible in real-time under fluoroscopy (FIG. 22A) achieving instant hemostasis, with subsequent DSA showing absence of flow in the embolized artery (FIG. 7A to 7C). Pigs were euthanized at one-hour-post-embolization. All embolized arteries were harvested for micro-CT and histologic evaluation. On micro-CT, pocBEM entirely occluded the lumen of the iliac artery (FIG. 7D and FIGS. 22B and 22C). On histology images, pocBEM appeared as an amorphous intravascular material (FIGS. 22D and 22E). Moreover, to compare pocBEM with a clinically used embolic agent, coil embolization of IIA was performed (FIGS. 7E and 7F). Following unsuccessful embolization with endovascular coils in an anticoagulated state, delivery of 1-2 cc of pocBEM to the coil mass was able to achieve instant hemostasis rescuing the failed coils (FIG. 7G). Furthermore, FIG. 7H demonstrates that in the event of an accidental, non-target delivery of pocBEM, pocBEM could be retrieved using the Penumbra Aspiration catheter system to restore blood flow. On high resolution micro-CT, harvested iliac arteries from FIG. 7H showed extensive streak artifact caused by the coils and no evidence for residual pocBEM, suggesting that the material was successfully aspirated from the LIIA (FIG. 7I).

Next, renal artery embolization was performed using pocBEM with subsequent DSA images showing complete cessation of blood flow into the kidney (FIGS. 22F and 22G). However, coil embolization of the renal artery failed to achieve hemostasis; while 1-2 cc of pocBEM delivery into the coil mass in the renal artery was able to achieve instant hemostasis (FIGS. 7J and 7K). Following harvest of the embolized kidneys, high resolution micro-CT imaging was performed. Kidneys embolized with pocBEM alone demonstrated uniform filling of the main renal artery and segmental branches without causing any imaging artifacts (FIG. 22H). In histology, pocBEM was present in hilar and segmental arterial branches in the embolized kidney (FIG. 22I). Micro-CT imaging of the renal artery that received both coils and pocBEM again demonstrated significant streak artifact from the coils and uniform casting of the pocBEM embolized segments of the renal artery (FIG. 7L).

Together, these results demonstrate that BEMs can trigger an enhanced local cellular proliferation, promote vascularity, and biodegradation. These results also demonstrate that a fibroinflammatory response can maintain long term occlusion and prevent recanalization and fragmentation.

Experimental Section

Platelet Rich Fibrin (PRF) and Lyophilized PRF (L-PRF) Preparation:

To generate PRF and L-PRF, blood samples were collected from healthy adult Yorkshire pigs. In a typical preparation, 10 mL whole blood was collected into a glass blood tube with no additives (BD Vacutainer, BD, Franklin Lakes, NJ, USA), followed by immediate centrifugation at 2700 rpm for 12 minutes at room temperature. After centrifugation, blood was separated into two distinct phases including straw-colored top layer PRF, and red blood rich mass at the bottom of the tube. The top PRF layer was carefully collected, frozen at −80° C., and lyophilized for 24 hours (Labconco FreeZone, Kansas City, USA) to obtain L-PRF.

Polyacrylamide Gel Electrophoresis (SDS PAGE):

Gel electrophoresis was performed to fractionate L-PRF solubilized in protein extraction buffer under reducing conditions using a 8-16% polyacrylamide gel (Bio-Rad Laboratories, Hercules, CA, USA). Total protein concentration in each sample was measured using BCA protein assay (Thermo Fisher Scientific, Waltham, MA, USA), and 20 μg total protein was loaded into each well. Precision Plus Protein™ Dual Color Standards (Bio-Rad Laboratories, Hercules, CA, USA) was used to identify molecular weight of protein fractions. Gels were resolved at 100 volts for 1 hour followed by Coomassie blue R-250 staining (Imperial™ Protein stain, Thermo Fisher Scientific, Waltham, MA, USA). Gel and proteins were separated by electrophoresis at 100V for 1 hour. Gels were imaged using Amersham imager 680 (Global Life Sciences Solutions USA LLC, MA, USA). Samples were tested in triplicates.

Western Blotting:

VEGF-A, PDGF-B, and TGF-β proteins were detected using Western blotting. PRF and L-PRF samples were loaded into 8-16% polyacrylamide gel (Bio-Rad Laboratories, Hercules, CA, USA) in Tris-glycine-SDS buffer (Invitrogen, Carlsbad, CA, USA) and ran under reducing conditions at 100 V for 1 hour. Proteins were transferred to nitrocellulose membranes (Bio-Rad Laboratories, Hercules, CA, USA) followed by blocking with 5% BSA solution in PBS overnight at 4° C. Membranes were then incubated with antibodies specific for VEGF (Abcam; ab53465: 1:1000), PDGF (Abcam; ab3404; 1:1000) or TGF-β (Abcam; ab92486; 1:1000) for one hour at room temperature followed by incubation with respective HRP-conjugated secondary antibody (ab97110 for PDGF; ab97051 for TGF-β and VEGF) for one hour at room temperature. Membranes were washed three-times with PBS supplemented with 1% tween 20 for 10 minutes after each incubation period. Specific protein bands were visualized by incubating the membranes with an aliquot of Supersignal westfemto maximum sensitivity reagent substrate (Thermo Fisher Scientific, MA, USA). Three independent western blotting experiments were conducted for each growth factor.

Enzyme-Linked Immunosorbent Assay (ELISA):

L-PRF preparation was solubilized at 6 mg per 1 mL of serum free DMEM media at 37° C. for 1 hour then centrifuged at 500×g for 1 minute then stored at −80° C. until analysis. The L-PRF extract was analyzed for the protein levels of VEGF-A (RAB1135-1KT, Sigma-Aldrich, St. Louis, MO, USA) and PDGF-B (Porcine PDGF-BB ELISA, RayBiotech, GA, USA) using ELISA kits according to manufacturer's instructions.

Cell Culture:

L929 cells were obtained from American Type Culture Collection (ATCC, Manassas, VA, USA) and cultured in minimum essential medium (MEM) supplemented with 10% (v/v) fetal bovine serum (FBS), 1% Penicillin/streptomycin and incubated in a humidified 5% $CO_2$ at 37° C.

Extraction Preparation:

PRF and L-PRF were incubated in serum free MEM supplemented with antibiotics in a 37° C. inside a water bath for 72 hours. Cells and debris free extract were collected by centrifuging at 5000 rpm for 15 minutes.

Cell Proliferation:

The proliferation of L929 cells was assessed with WST-1 assay (Cayman chemicals, Ann Arbor, MI, USA). Cells were plated in 96 well plates at a density of 2000 cells per well and incubated for 24 hours. Cell media was changed to low serum (0.5% FBS) MEM for 24 hours to induce growth arrest. Cells were then incubated with PRF extracts for up to 3 days. Cell viability was assessed at day 1 and day 3 post-treatment. Experiments were done in six replicated and repeated independently three times.

Cell Migration:

Cells were fluorescently labeled with cell tracker green (Invitrogen, Carlsbad, CA, USA) and plated at 20,000 cells density per chamber (Ibidi USA Inc., Fithcburg, WI, USA) and incubated in minimum essential medium (MEM) supplemented with 10% (v/v) fetal bovine serum (FBS), 1% Penicillin/streptomycin and incubated in a humidified 5% $CO_2$ at 37° C. chamber for 24 hours. Inserts were then removed creating a monolayer of fluorescently-labeled cells to expose the cell-free wound area. Cell were then washed with warm PBS and treated with PRF or L-PRF extracts or serum free media (negative control), or complete growth medium (positive control). Cell migration was assessed following incubation with 24 hours. Fluorescence images were taken at 0 and 24 hours post treatment. Migrated cells within the wound area were counted using Image J software (National Institutes of Health, Bethesda, MD, USA). Data was calculated as fold change of cell migration relative to negative control. Three independent migration experiments were performed.

Blood-Derived-Embolic Material (BEM) Preparation:

BEMs were prepared by mixing nanoclay and L-PRF at predetermined ratios (Table 1). Nanoclay (NC) (9% w/v) was first prepared by mixing Laponite® powder (BYK Additives Ltd.) in ice cold ultrapure water using a speed mixer (FlackTek, Inc., Landrum, SC, USA). L-PRF was then added into NC to generate different BEM formulations (Table 1). For instance, 9 wt % BEM was prepared by adding 250 mg lyophilized PRF and 2.5 g water into 7.5 g 9% (w/v) NC, followed by mixing in the speed mixer to achieve homogenization. Final 9 wt % BEM contained 6.6 wt % NC and 2.4 wt % L-PRF. Other BEMs were prepared using similar protocol. To render the gel radiopaque, ethiodized oil contrast agent (Lipiodol® Ultrafluide, Laboratoire Guerbet, Aulnay-Sous-Bois, France) was mixed with the BEM keeping all solid components weights consistent to create a BEM-ethiodized oil (BEM-EO) formulation that contains 25 wt % final concentration of ethiodized oil.

Point-of-Care BEM (pocBEM) Preparation:

A rapid preparation protocol was developed to produce a pocBEM for point-of-care applications. In this process, 10 mL whole blood was collected into a glass tube and immediately centrifuged at 700 rpm at room temperature for 3 minutes to generate an upper phase of injectable platelet rich fibrin (I-PRF). The upper phase (I-PRF) was aspirated into a syringe then weighed. Five grams of injectable PRF was immediately mixed with 9% (w/v) NC (15 g) and ethiodized oil (20 wt %) using a speed mixer to generate a pocBEM composition. The process was timed (n=5) to investigate the feasibility and applicability of generating a pocBEM from the pig, followed by endovascular embolization of iliac or renal artery using an embolic agent derived from blood aliquot obtained from the same animal in a timely fashion.

Rheological Evaluation of NC, BEMs, and pocBEMs:

Rheological testing of NC, BEMs, and pocBEMs were performed using a rotational rheometer (MCR 302, Anton Paar, Austria). All rheology measurements were carried out using a 25 mm sandblasted upper plate with the gap between the bottom (also sandblasted), and the upper plates was kept at 0.8 mm. For each test, the temperature was equilibrated at 37° C. for 5 minutes before the measurements were taken. During testing, a solvent trap was used, and the edge of the solvent trap was filled with water to provide humidified environment to prevent the materials from drying. Flow curves were performed using shear rate range of $10^{-3}$ $s^{-1}$ and 100 $s^{-1}$. Large amplitude oscillation sweeps (LAOS) were performed at a fixed angular frequency of 10 rad $s^{-1}$ for all materials. Thixotropy tests were performed to investigate the materials' recoverability during structural decomposition and recovery as a function of time. The strain was oscillated between low-magnitude at 0.1% for 2.5 minutes and high-magnitude at 100% for 1 minute at 10 rad $s^{-1}$. Each type of test was run in triplicate.

Scanning Electron Microscopy (SEM):

SEM was performed to investigate microstructure of NC, BEMs, and pocBEMs following lyophilization. The freeze-dried specimens were coated with 6 nm gold/palladium layer using a sputter coater (LEICA EM ACE200, Wetzlar, Germany), followed by SEM imaging (JCM-6000PLUS, JEOL Ltd., Peabody, MA, USA).

Injection Force:

Catheter injectability of materials were assessed by measuring the injection force using compression testing (Instron 5942, Instron Corp., Norwood, MA, USA). The materials were loaded into 1 mL Medallion syringes (Merit Medical Systems, Inc., South Jordan, UT, USA), and the force required to push the material through a 100 cm 5 F catheter (Cook Medical, Bloomington, IN, USA) at a flow rate of 300 μL $min^{-1}$ was recorded using system software (Bluehill3, Instron Corp., Norwood, MA, USA). Each sample was tested three times. The maximum forces during the injection process were analyzed and summarized.

Ex Vivo Occlusion-Displacement Test:

The ability of NC, BEM, BEM-EO compositions to withstand against hydrostatic pressure was assessed using occlusion-displacement test. Briefly, 1 mL of material was placed in a tube to mimic embolization of a blood vessel. PBS was infused at constant flow of 70 mL mini (GenieTouch™ syringe pump system, Kent Scientific Corporation, CT, USA) to displace the material. The pressure during material displacement was recorded using a pressure sensor (Omega, PX 409, CT, USA) that was connected to the upstream and downstream of the material. Three tests were performed for each material, and the maximum recorded pressure was summarized.

Sterility Test:

To assess the gel's sterility, an aliquot of BEM-EO and pocBEM extracts were solubilized in LB broth using an orbital shaker for 24 hours or 1 week at 37° C. at 180 RPM. Inoculation of LB broth with *Escherichia coli* bacteria (*E. coli*) were used as positive control. The optical density of the 200 μL aliquot of each LB solutions was measured at 600 nm using a microplate reader (SpectraMax iD5, Molecular Devices, LLC. CA, USA). Additionally, Mueller Hinton agar plates (Thermo Scientific Remel Mueller Hinton Agar, R454082, MA, USA) were used to further rule out assess bacterial growth of each aliquot following incubation for 1 week. Agar plates were incubated at 37° C. for 24 hours following inoculation.

Cytotoxicity:

The cytotoxicity of all biomaterial was assessed in L929 cells accordingly to International Standard (ISO 10993) protocol using WST-1 assay (Caymen chemicals, Ann Arbor, MI, USA). Cells were plated in 96 well plates at a density of 5000 cells per well and incubated for 24 hours. Cells were then treated with PRF, L-PRF, BEM, and BEM-EO extracts following dilution with MEM growth medium at different concentrations (100%, 50%, 25%, 12.5% (v/v)). Cell viability was assessed at 24 hours using WST-1 assay (Caymen chemicals, Ann Arbor, MI, USA), according to manufacturer's instructions. Three independent experiments were performed with four replicates in each experiment.

Clotting Test:

The hemostatic ability of a BEM-EO composition in 96-well plate and rheological hemostatic tests was performed as described elsewhere (Gaharwar et al., ACS Nano., 8:9833 (2014)). Time-dependent modulus change of blood was done either using blood aliquot alone or in contact with pocBEM, or BEM-EO using a rotational rheometer (MCR 302, Anton Paar, Austria).

Figure 13:
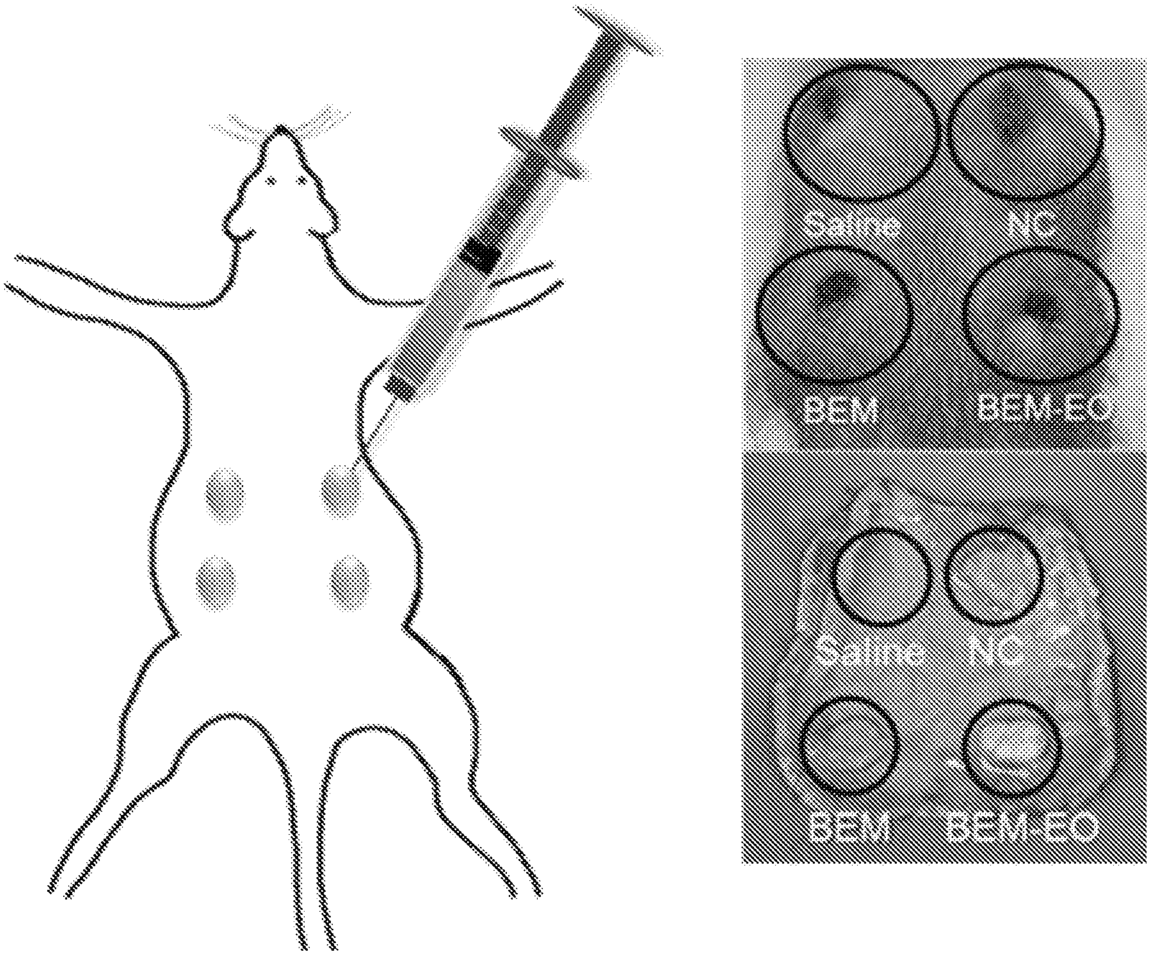
FIG. 13. Subcutaneous injection of saline, NC, BEM and BEM-EO in the dorsum of rats. Each rat received four 200 μL subcutaneous injections of each of saline, NC, BEM, and BEM-EO (n=4, each group).
Figure 14:
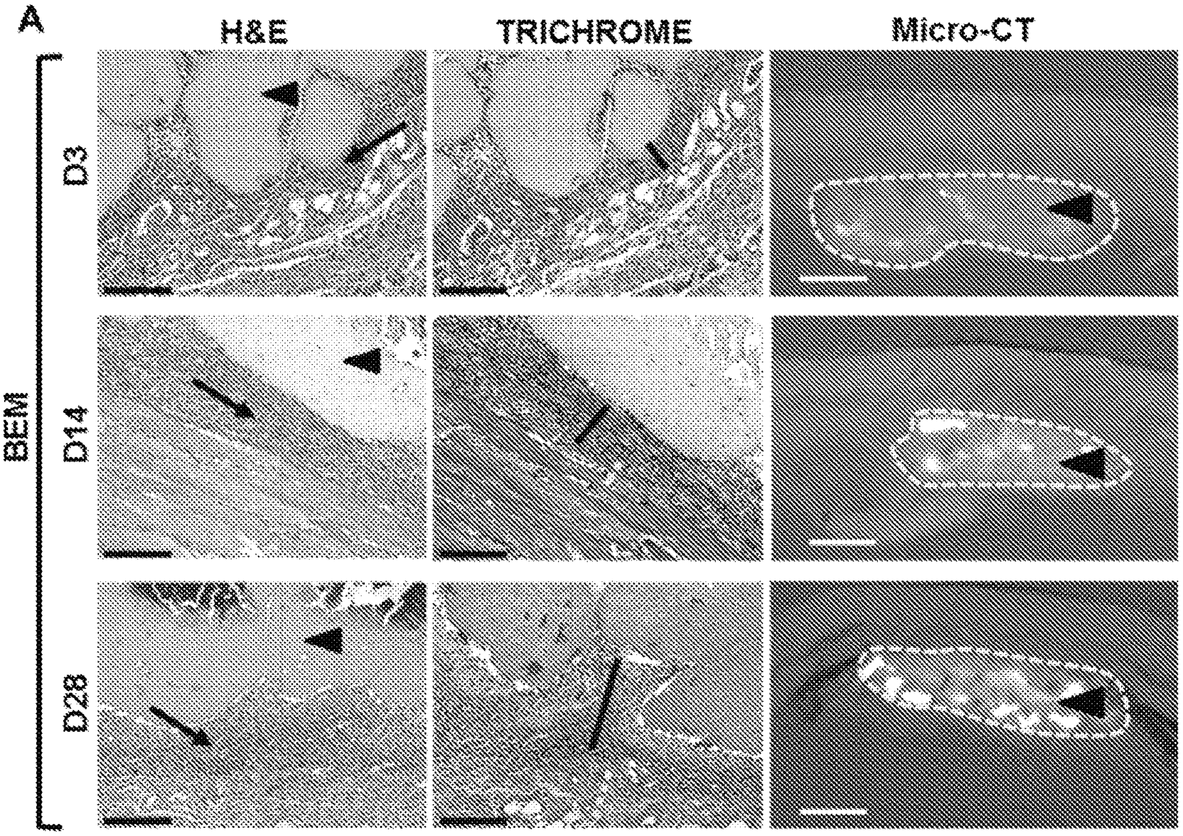
FIGS. 14A-14E. Morphometric analysis of subcutaneously injected BEM in the rat dorsum.
Figure 14:
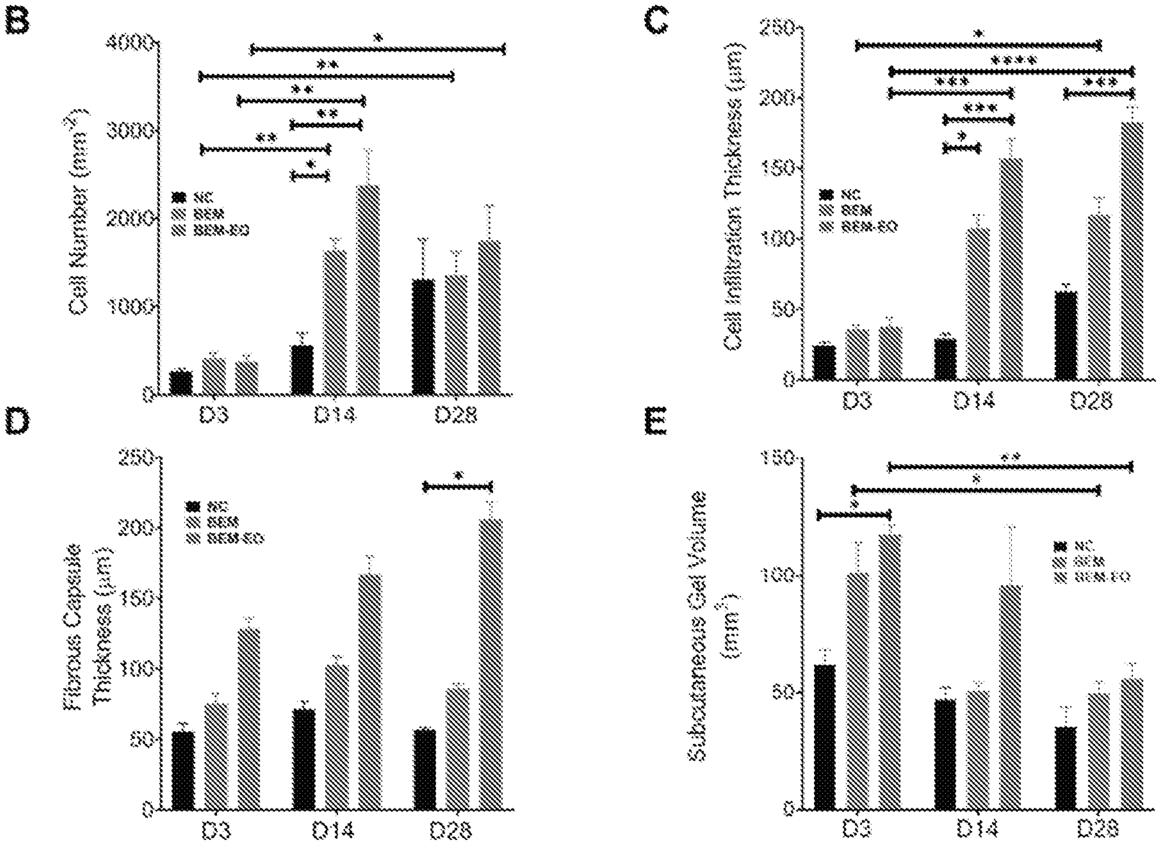

In Vivo Rat Model:

Four subcutaneous injections of NC, BEM, and BEM-EO compositions were performed on the dorsum of 4 to 5 week old male Sprague Dawley rats (Charles River Laboratories, Wilmington, MA) under isoflurane anesthesia (FIG. 13). Each injection site received 0.2 mL of each biomaterial. Subgroups of rats were euthanized at 3, 14, or 28 days post-injection (n=4 per group).

In Vivo Porcine Model:

Prior to the experiment, Yorkshire pigs (S&S Farms, Brentwoods, CA) were housed for 4 days to acclimate. Intramuscular injection of 5 mg $kg^{-1}$ tiletamine-zolazepam (Telazol, Zoetis, NH, USA), 2 mg $mL^{-1}$ Xylazine, and 0.02 mg $kg^{-1}$ Glycopyrrolate were performed to induce anesthesia. Prior to operation, pigs were positioned supine and intubated on angiography table (Pannomed Aeron, DRE, KY). During the procedure, anesthesia was sustained with inhalation of 1.5-3% isoflurane, and electrocardiogram, transcutaneous oxyhemoglobin saturation ($SpO_2$), end-tidal $CO_2$ concentration, inspired oxygen fraction, and core temperature also were monitored. Using ultrasound (ACUSON 52000, Siemens, Germany) and fluoroscopy (OEC9800 plus C-Arm, GE Healthcare Systems, Chicago, IL, USA) guidance, percutaneous access to the carotid artery was achieved using a standard 21 G access needle and 0.018 inch stiff guide wire. This wire was exchanged for a 0.035 Bentson wire, and a 5 French vascular sheath was placed. Using a combination of 5 Bernstein catheter (Cook Medical, Bloomington, IN, USA) and an 0.035 guidewire (Cook Medical, Bloomington, IN, USA), the tip of the catheter was positioned at the target arteries; position was confirmed using DSA (350 mgI $mL^{-1}$ Omnipaque, GE HealthCare, MA). BEM-EO or pocBEM compositions containing 1 mL Medallion syringes were connected to the catheter via Luer-lock and injected over 15-20 seconds into the iliac or renal artery during real-time fluoroscopy guidance. After embolization with a BEM-EO or pocBEM composition, multiple hand injected DSA was performed to evaluate blood flow into embolized artery. Following embolization, pigs were euthanized either at 1 hour (non-survival group) or 2 weeks post-embolization (survival group). Blood samples were obtained for analysis before and after the surgery. CT angiography (CTA) scans were done 2 weeks after embolization in the survival group. Arteries embolized with BEM-EO or pocBEM and kidneys were harvested for micro-CT imaging and histopathology analysis.

Complete Blood Count (CBC) and Blood Biochemistry:

Veterinary hematology analyzer (HemaTrue, Heska, Loveland, CO, USA) was used to analyze CBC. Biochemistry was carried out by Veterinary Chemistry Analyzer (DRI-CHEM 4000, Heska, Loveland, CO, USA). Measured CBC and biochemistry values were used for assessing the overall health of the pigs. Also, CBC was done for rats as described. The pig serum samples were analyzed using a porcine cytokine array 13-plex (Eve Technologies, Calgary, CA, USA).

Computed Tomography Angiography (CTA):

Dual energy CT scanner was used (Siemens Force, Siemens, Erlangen, Germany) for whole-body imaging of the pigs. During CT scanning, standard thin-cut CT angiography was performed before and after injection of 120 mL of IV contrast agent (Omnipaque 350 mgI $mL^{-1}$, GE HealthCare, MA, USA). The CT scan was performed at 80 kVp to 150 kVp energy levels with 0.6 mm detector size configuration. Following CT scans, 3D reconstruction, volumetric studies, and image analysis as well as image interpretation was performed using Visage 7.11 PACS system (Visage Imaging Inc., San Diego, CA, USA).

Histology Studies:

Tissue samples were embedded into paraffin blocks; 4 μm sections were stained with H&E, Mason's trichrome, and EVG elastic stain, and immunostaining for PCNA (ab92552, Abcam, Cambridge, MA, USA) and CD31 (ab182981) was performed. Morphometric analysis of histology slides was performed using ImageJ software (National Institutes of Health) including total cell number in the subcutaneously injected skin tissue, and the number of PCNA positive cells was counted in 8 randomly selected fields that measured 0.1 $mm^2$ area in each tissue section. Fibrous capsule thickness and cell infiltration thickness were measured in Mason's trichrome stained sections. On the epidermis side of each injected site, 12 random locations were selected per sample to measure the thickness of the fibrous capsule and the thickness of cell infiltration layer that formed following biomaterial injection. The number of vessels around the subcutaneous injection area was manually counted in 8 randomly selected high-power fields (400-fold magnification) per sample.

Micro-CT Imagining:

Micro-CT imaging was performed using Skyscan 1276 (Bruker, Kontich, Belgium). Scanning parameters were 55 kV, 200 μA, 80 μm resolution using a 0.5 mm aluminum (Al)

filter and 0.8° rotational step for kidney samples. The scanning parameters of 45 kV, 200 μA energy level, 20 μm resolution with 0.25 Al filter and 0.4° rotational step were used for iliac artery samples. BEM-EO filled air tight tubes were scanned at 50 kV, 200 μA energy level, 20 μm resolution with Al 0.25 mm filter and 0.6° rotational step. Micro-CT reconstruction of each scan was performed using NRecon software (Bruker, Kontich, Belgium). BEM-EO volume in embolized iliac arteries was calculated by thresholding the reconstructed micro-CT images using Mimics segmentation software (Materialise, Leuven Belgium). Scanned BEM-EO filled air locked tubes samples were analyzed using CTan software (CT Analyzer, Bruker, Kontich, Belgium).

Statistical Analysis:

All data reported as average±SEM, unless otherwise stated. Statistical differences between multiple groups was calculated using analysis of variance (ANOVA) with Tukey post-test or Dunnett's multiple comparisons tests. Student t-test was used to calculate statistical differences between two groups using Prism Software v8 (GraphPad, CA, USA). $p<0.05$ was considered to be significant.

Example 2: Treating Hemodynamic Instability with BEM

Figure 23:
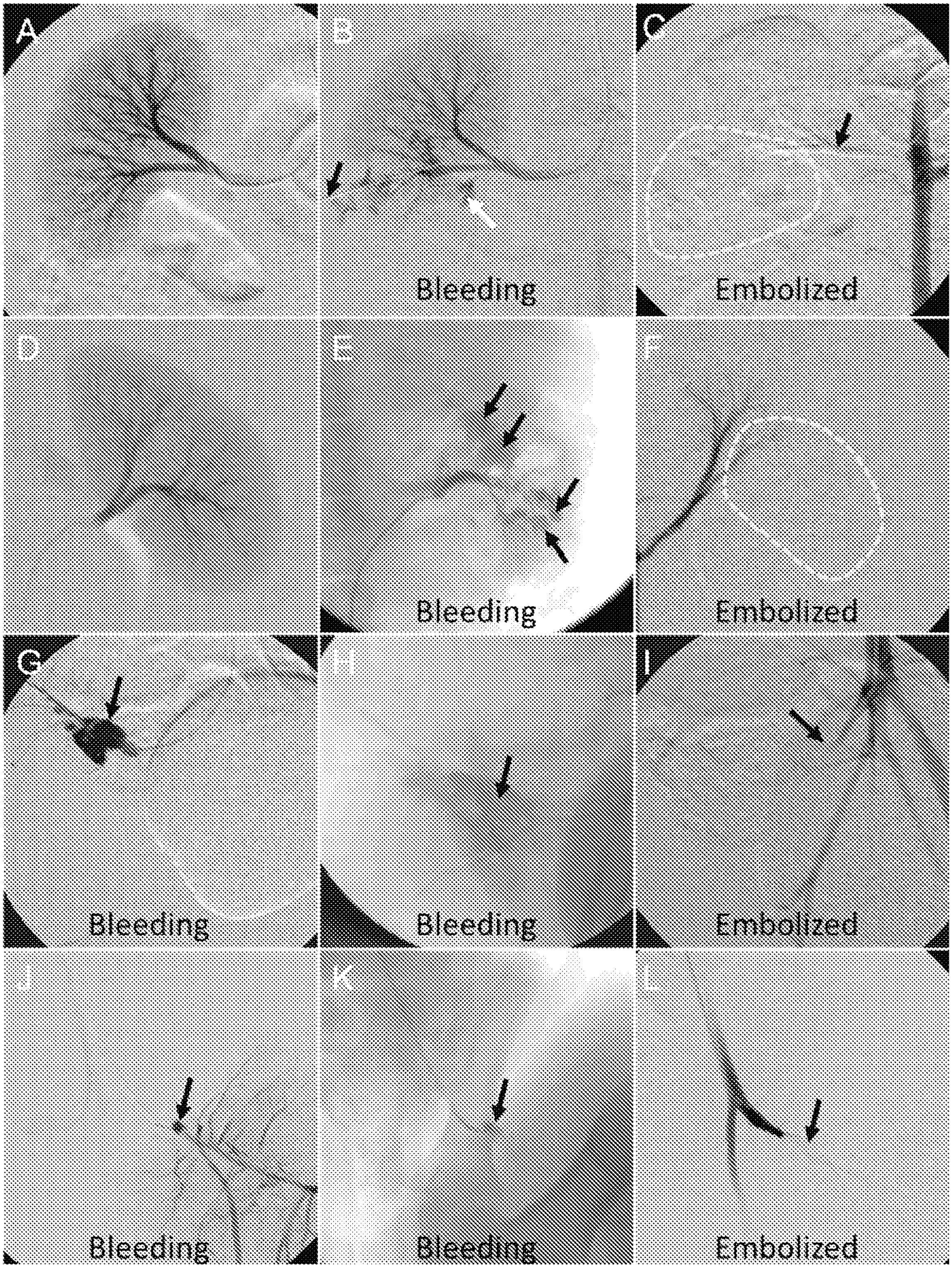
FIGS. 23A-23L. Acute bleeding control with catheter directed embolization of injured arteries in porcine model.

To test the value of pocBEM in acute hemorrhage, direct injury to kidneys and pelvic vessels or pigs were induced using 20 cm 18 G needle (FIG. 23). In two kidneys, significant injury including pseudoaneurysms as well as active extravasation (FIG. 23A to 23F) was produced using a needle under ultrasound and fluoroscopic guidance. Animals subsequently became hemodynamically unstable, tachycardic and hypotensive; immediately, these animals received pocBEM to achieve hemostasis and restore hemodynamic stability (FIGS. 23C and 23F). In another two animals, bleeding arterial pseudoaneurysms were created in pelvic vessels such as branches of external iliac artery (FIG. 23G to 23L). These branches were subsequently embolized (FIGS. 231 and 23L) to restore hemodynamic stability.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising (a) platelet-rich fibrin (PRF) or leukocyte-PRF and (b) one or more nanoclay materials.

2. The composition of claim 1, wherein said composition comprises said PRF and said leukocyte-PRF.

3. The composition of claim 1, wherein said composition comprises from about 0.1 wt % to about 90 wt % of said PRF.

4. The composition of claim 1, wherein said composition comprises from about 0.1 wt % to about 90 wt % of said leukocyte-PRF.

5. The composition of claim 1, wherein said composition comprises from about 0.4 to about 0.8 wt % of said PRF.

6. The composition of claim 1, wherein said composition comprises from about 1.2 to about 1.6 wt % of said PRF.

7. The composition of claim 1, wherein said composition comprises from about 2.2 to about 2.6 wt % of said PRF.

8. The composition of claim 1, wherein said composition comprises from about 0.5 wt % to about 90 wt % of said nanoclay material.

9. The composition of claim 8, wherein said composition comprises from about 6.4 to about 6.8 wt % of said nanoclay material.

10. The composition of claim 1, wherein said nanoclay material is a silicate nanoclay.

11. The composition of claim 1, said composition further comprising a radiopaque contrast agent.

12. The composition of claim 11, wherein said composition comprises from about 0.1 wt % to about 90 wt % of said radiopaque contrast agent.

13. The composition of claim 12, wherein said composition comprises from about 10 to about 40 wt % of said radiopaque contrast agent.

14. The composition of claim 11, wherein said radiopaque contrast agent is selected from the group consisting of ethiodized oil, iohexol, gadobutrol, iron oxide nanoparticles, zinc oxide nanoparticles, magnesium oxide particles, and tantalum particles.

15. The composition of claim 1, wherein the viscosity of said composition decreases under a shear rate of about 10-2 1/second.

16. The composition of claim 1, wherein said composition has a displacement pressure of from about 85 kPa to about 200 kPa.

17. A method for embolization of a blood vessel within a mammal, wherein said method comprises delivering, to said blood vessel, a composition according to claim 1.

18. A method for reducing blood flow in a blood vessel within a mammal, wherein said method comprises delivering, to said blood vessel, a composition according to claim 1.

19. The method of claim 18, wherein said blood flow in said blood vessel is reduced to less than about 1 mL/second.

* * * * *